(12) United States Patent
Yang et al.

(10) Patent No.: US 11,180,785 B2
(45) Date of Patent: Nov. 23, 2021

(54) COMPOSITION FOR PRODUCING TAGATOSE AND METHOD OF PRODUCING TAGATOSE USING THE SAME

(71) Applicant: CJ CheilJedang Corporation, Seoul (KR)

(72) Inventors: Sungjae Yang, Suwon-si (KR); Young Mi Lee, Suwon-si (KR); Il Hyang Park, Suwon-si (KR); Hyun Kug Cho, Suwon-si (KR); Seong Bo Kim, Seongnam-si (KR); Chan Hyoung Lee, Suwon-si (KR); Eun Jung Choi, Seongnam-si (KR)

(73) Assignee: CJ CheilJedang Corporation, Seoul (KR)

( * ) Notice: Subject to any disclaimer, the term of this patent is extended or adjusted under 35 U.S.C. 154(b) by 0 days.

(21) Appl. No.: 16/498,237

(22) PCT Filed: Mar. 30, 2018

(86) PCT No.: PCT/KR2018/003768
§ 371 (c)(1),
(2) Date: Sep. 26, 2019

(87) PCT Pub. No.: WO2018/182354
PCT Pub. Date: Oct. 4, 2018

(65) Prior Publication Data
US 2020/0024627 A1    Jan. 23, 2020

(30) Foreign Application Priority Data

| Mar. 31, 2017 | (KR) | 10-2017-0042166 |
| Aug. 31, 2017 | (KR) | 10-2017-0111489 |
| Aug. 31, 2017 | (KR) | 10-2017-0111494 |
| Nov. 24, 2017 | (KR) | 10-2017-0158765 |

(51) Int. Cl.
*C12P 19/02* (2006.01)
*C12P 19/24* (2006.01)

(52) U.S. Cl.
CPC .............. *C12P 19/02* (2013.01); *C12P 19/24* (2013.01); *C12Y 207/01002* (2013.01); *C12Y 401/0204* (2013.01)

(58) Field of Classification Search
None
See application file for complete search history.

(56) References Cited

FOREIGN PATENT DOCUMENTS

| CN | 106399427 A | 2/2017 |
| EP | 3211078 A1 | 8/2017 |
| KR | 10-744479 | 7/2007 |
| KR | 10-0964091 | 6/2010 |
| KR | 10-1057873 | 8/2011 |
| KR | 10-1368731 | 2/2014 |
| KR | 10-2014-0143109 A | 12/2014 |
| KR | 10-1480422 | 1/2015 |
| KR | 10-1550796 | 9/2015 |
| WO | WO 2006/058092 A2 | 6/2006 |

OTHER PUBLICATIONS

Lee et al., "Structure-based prediction and identification of 4-epimerization activity of phosphate sugars in class II aldolases", Nautre Scientific Reports, May 2017, 7:1934. DOI:10.1038/s41598-017-02211-3.*
NCBI Reference Sequence: WP_012548536.1, May 25, 2013, "tagatose-6-phosphate kinase [*Dictyoglomus thermophilum*]", 1 page.
International Search Report and Written Opinion of the International Patent Application No. PCT/KR2018/003768, dated Jul. 30, 2018 and the English translation of the International Search Report; 13 pages.
Brinkkötter et al., "Two class IID-tagatose-bisphosphate aldolases from enteric bacteria", Arch Microbiol, 2002, vol. 177, pp. 410-419.
NCBI, GenBank accession No. WP_015868068.1, Jun. 16, 2015; 1 page.
Wichelecki et al., "ATP-binding Cassette (ABC) Transport System Solute-binding Protein-guided Identification of NovelD-Altritol and Galactitol Catabolic Pathways in Agrobacterium tumefaciens C58", The Journal of Biological Chemistry, Nov. 27, 2015, vol. 290, No. 48, pp. 28963-28976.
The extended European search report for EP Patent application No. 18775140.9 dated Dec. 17, 2020.
Lee et al., "High-yield production of pure tagatose from fructose by a three-step enzymatic cascade reaction", Biotechnol Lett (2017) 39:1141-1148.
Lee et al., "Structure-based prediction and identification of 4-epimerization activity of phosphate sugars in class II aldolases", Scientific Reports | 7: 1934 | DOI:10.1038/s41598-017-02211-3; 9 pages, 2017.
Database EMBL; Kantor R.S. et al: "Acidobacteriales bacterium 59-55 D-tagatose-bisphosphate aldolase, class II, non-catalytic subunit", Jan. 27, 2017, XP055755572.
Database UniProt; "SubName: Full=D-tagatose-1,6-bisphosphate aldolase subunit GatZ/KbaZ {ECO:00003131 EMBL:SDF07868.1};", Apr. 12, 2017, XP055755584.
Database UniProt; "SubName: Full=D-tagatose-bisphosphate aldolase class II accessory protein AgaZ {ECO:00003131 EMBL:ACR79402.1};", Jul. 28, 2009, XP55752014.
Database UniProt; "SubName: Full=D-tagatose-bisphosphate aldolase class II accessory protein AgaZ {ECO:00003131 EMBL:EH042442.1}; SubName: Full=Tagatose-bisphosphate aldolase noncatalytic subunit {ECO:00003131 EMBL:APF18436.1};", Mar. 21, 2012, XP055755573.
Database UniProt; "SubName: Full=D-tagatose-bisphosphatealdolase class II accessory protein AgaZ {ECO:00003131 EMBL:ADQ45460.1};", Feb. 8, 2011, XP055755578.
Database UniProt; "SubName: Full=Putative tagatose 6-phosphate aldolase subunit Z {ECO:00003131 EMBL:BAM00345.1};", Jun. 13, 2012, XP055755583.

(Continued)

*Primary Examiner* — Suzanne M Noakes
(74) *Attorney, Agent, or Firm* — Squire Patton Boggs (US) LLP

(57) ABSTRACT

Provided are a composition for producing tagatose, comprising fructose-4-epimerase, and a method of producing tagatose using the same.

2 Claims, 9 Drawing Sheets

Specification includes a Sequence Listing.

(56) References Cited

OTHER PUBLICATIONS

Database UniProt; "SubName: Full=Tagatose-1, 6-bisphosphate aldolase non-catalytic subunit AgaZ/GatZ (ECO:00003131EMBL:SHK57980.1);", Mar. 15, 2017, XP055752016.
Database UniProt; "SubName: Full=Tagatose-bisphosphate aldolase {ECO:00003131 EMBLBAS28167.1 };", Nov. 11, 2015, XP055752017.
Database UniProt; "SubName: Full=Uncharacterized protein {ECO:00003131EMBL:KPL84211.1};", Jan. 20, 2016, XP055755301.
Database UniProt; "SubName: Full=Uncharacterized protein {ECO:00003131 EMBLACY49419.1};", Dec. 15, 2009, XP055752015.

* cited by examiner

SEQUENCE LISTING

```
<160> NUMBER OF SEQ ID NOS: 22

<210> SEQ ID NO 1
<211> LENGTH: 426
<212> TYPE: PRT
<213> ORGANISM: Artificial Sequence
<220> FEATURE:
<223> OTHER INFORMATION: An amino acid sequence of Tagatose-biphosphate
      aldolase, CJ_TD_F4E derived from Thermanaerothrix daxensis

<400> SEQUENCE: 1

Met Val Thr Tyr Leu Asp Phe Val Val Leu Ser His Arg Phe Arg Arg
1               5                   10                  15

Pro Leu Gly Ile Thr Ser Val Cys Ser Ala His Pro Tyr Val Ile Glu
            20                  25                  30

Ala Ala Leu Arg Asn Gly Met Met Thr His Thr Pro Val Leu Ile Glu
        35                  40                  45

Ala Thr Cys Asn Gln Val Asn Gln Tyr Gly Gly Tyr Thr Gly Met Thr
    50                  55                  60
```

```
Pro Ala Asp Phe Val Arg Tyr Val Glu Asn Ile Ala Ala Arg Val Gly
 65                  70                  75                  80

Ser Pro Arg Glu Asn Leu Leu Leu Gly Gly Asp His Leu Gly Pro Leu
                 85                  90                  95

Val Trp Ala His Glu Pro Ala Glu Ser Ala Met Glu Lys Ala Arg Ala
            100                 105                 110

Leu Val Lys Ala Tyr Val Glu Ala Gly Phe Arg Lys Ile His Leu Asp
        115                 120                 125

Cys Ser Met Pro Cys Ala Asp Asp Arg Asp Phe Ser Pro Lys Val Ile
    130                 135                 140

Ala Glu Arg Ala Ala Glu Leu Ala Gln Val Ala Glu Ser Thr Cys Asp
145                 150                 155                 160

Val Met Gly Leu Pro Leu Pro Asn Tyr Val Ile Gly Thr Glu Val Pro
                165                 170                 175

Pro Ala Gly Gly Ala Lys Ala Glu Ala Glu Thr Leu Arg Val Thr Arg
            180                 185                 190

Pro Glu Asp Ala Ala Glu Thr Ile Ala Leu Thr Arg Ala Ala Phe Phe
        195                 200                 205

Lys Arg Gly Leu Glu Ser Ala Trp Glu Arg Val Val Ala Leu Val Val
    210                 215                 220

Gln Pro Gly Val Glu Phe Gly Asp His Gln Ile His Val Tyr Arg Arg
225                 230                 235                 240

Glu Glu Ala Gln Ala Leu Ser Arg Phe Ile Glu Ser Gln Pro Gly Leu
                245                 250                 255

Val Tyr Glu Ala His Ser Thr Asp Tyr Gln Pro Arg Asp Ala Leu Arg
            260                 265                 270

Ala Leu Val Glu Asp His Phe Ala Ile Leu Lys Val Gly Pro Ala Leu
        275                 280                 285

Thr Phe Ala Phe Arg Glu Ala Val Phe Ala Leu Ala Ser Ile Glu Asp
    290                 295                 300

Trp Val Cys Asp Ser Pro Ser Arg Ile Leu Glu Val Leu Glu Thr Thr
305                 310                 315                 320

Met Leu Ala Asn Pro Val Tyr Trp Gln Lys Tyr Tyr Leu Gly Asp Glu
                325                 330                 335

Arg Ala Arg Arg Ile Ala Arg Gly Tyr Ser Phe Ser Asp Arg Ile Arg
            340                 345                 350

Tyr Tyr Trp Ser Ala Pro Ala Val Glu Gln Ala Phe Glu Arg Leu Arg
        355                 360                 365

Ala Asn Leu Asn Arg Val Ser Ile Pro Leu Val Leu Leu Ser Gln Tyr
    370                 375                 380

Leu Pro Asp Gln Tyr Arg Lys Val Arg Asp Gly Arg Leu Pro Asn Gln
385                 390                 395                 400

Phe Asp Ala Leu Ile Leu Asp Lys Ile Gln Ala Val Leu Glu Asp Tyr
                405                 410                 415

Asn Val Ala Cys Gly Val Arg Ile Gly Glu
            420                 425

<210> SEQ ID NO 2
<211> LENGTH: 1281
<212> TYPE: DNA
<213> ORGANISM: Artificial Sequence
<220> FEATURE:
<223> OTHER INFORMATION: DNA sequence of Tagatose-biphosphate aldolase,
      CJ_TD_F4E derived from Thermanaerothrix daxensis
```

<400> SEQUENCE: 2

```
atggttacct atttggattt tgtggtgctt tctcatcgtt ttaggcgccc cctgggcatt    60
acctcagtgt gttcggcgca tccgtatgtc attgaggcgg cgctgcgtaa tgggatgatg   120
acccatacac cggtcctaat cgaggccact tgcaatcaag tcaatcagta tggggggatat   180
acggggatga ccccggcaga tttcgtgcgg tatgtggaga atattgctgc acgggtaggc   240
tctccacgtg aaaacctcct tttgggtggc gatcatttgg accccctggt ctgggctcat   300
gaacctgctg agagtgccat ggaaaaagct cgagctctgg tcaaagccta tgtagaggct   360
ggttttcgca aaattcatct ggattgctca atgccctgtg cggatgatcg cgattttttct   420
ccaaaggtca ttgctgagcg ggcagccgaa ttggctcagg tggcagagtc aacttgtgat   480
gttatgggct tgcccttgcc caactacgtc attgaaccgg aggtgccccc agcaggtggc   540
gccaaggctg aagccgaaac tttgagggta acccgtccgg aggatgcagc ggagaccatt   600
gcactgacca gagcggcttt tttcaagcga ggtttagagt ctgcctggga acgtgtagtg   660
gcgttagtag tgcaacccgg tgttgaattc ggagatcatc agattcatgt ttaccgccgt   720
gaggaagcgc aggctctttc ccgcttcatt gaaagccagc ccggcttagt ctatgaggct   780
cactccaccg actatcagcc ccgtgatgcg ctgcgggctt tggttgagga tcatttcgca   840
atcctgaagg tgggtccggc gctaaccttt gcttttcgtg aggcagtttt tgccctggcc   900
agtatcgagg attgggtatg cgattcaccc agtcgcatcc tggaagtttt ggaaacaacc   960
atgctggcca acccggtcta ctggcaaaag tattacttgg gcgatgagcg agcgcgtcgg  1020
attgccagag ggtatagttt cagcgatcgc attcgttatt attggagtgc accagcggtt  1080
gaacaggcct tgaacgcttc gcgggcaaat ctgaatcgtg tttcgatccc ccttgtcctt  1140
ctcagtcagt atttgccgga tcaatatcgc aaagtgcggg atggacggct gcctaaccag  1200
tttgatgctt tgattctgga taaaatccaa gccgtactgg aagactacaa tgtggcgtgt  1260
ggtgtgagga tagggagtg a                                             1281
```

<210> SEQ ID NO 3
<211> LENGTH: 431
<212> TYPE: PRT
<213> ORGANISM: Artificial Sequence
<220> FEATURE:
<223> OTHER INFORMATION: An amino acid sequence of Tagatose-biphosphate aldolase, CJ_AB_F4E derived from Acidobacteriales bacterium

<400> SEQUENCE: 3

```
Met Ser Asp Asn Leu Gln Val Phe Leu Arg Glu Ser Arg Gly Arg Arg
1               5                   10                  15
Gly Ile Tyr Ser Val Cys Ser Ala His Pro Arg Val Ile Glu Ala Ala
                20                  25                  30
Met Arg Gln Ala Gly Ala Asp Gly Thr His Leu Leu Glu Ala Thr
            35                  40                  45
Ser Asn Gln Val Asn Gln Ala Gly Gly Tyr Thr Gly Met Thr Pro Ala
        50                  55                  60
Met Phe Arg Asp Tyr Val Tyr Asp Ile Ala Gln Glu Ile Gly Phe Asp
65                  70                  75                  80
Arg Ser Arg Leu Ile Leu Gly Gly Asp His Leu Gly Pro Asn Pro Trp
                85                  90                  95
Gln Gln Leu Asp Ala Ser Thr Ala Met Gln Tyr Ala Glu Glu Met Val
            100                 105                 110
```

Arg Leu Tyr Ile Glu Ala Gly Phe Thr Lys Ile His Leu Asp Ala Ser
            115                 120                 125

Met Arg Cys Ala Asp Ala Ala Ile Val Pro Asp Glu Val Met Ala
    130                 135                 140

Gly Arg Ala Ala Ala Leu Cys Ser Ala Ala Glu Ser Ala Arg Ala Arg
145                 150                 155                 160

Leu Gly Leu Ala Pro Val Val Tyr Val Ile Gly Thr Glu Val Pro Thr
                165                 170                 175

Pro Gly Gly Ala Ser His Ala Leu Asn Thr Leu Glu Val Thr Thr Arg
            180                 185                 190

Glu Ala Val Glu His Thr Leu Ser Val His Arg Lys Ala Phe His Asp
    195                 200                 205

Ala Gly Leu Asp Ala Ala Trp Gln Arg Val Ile Ala Val Val Gln
    210                 215                 220

Pro Gly Val Glu Phe Asp His Asp Ser Val Val Asp Tyr Asp Ala Ala
225                 230                 235                 240

Lys Ala Gly His Leu Gln Glu Phe Leu Gln Ala His Pro Glu Leu Val
                245                 250                 255

Met Glu Ala His Ser Ser Asp Tyr Gln Lys Pro Gln Ala Tyr Lys Glu
            260                 265                 270

Leu Val Arg Asp Gly Phe Ala Ile Leu Lys Val Gly Pro Ala Leu Thr
    275                 280                 285

Phe Ala Leu Arg Glu Met Leu Tyr Ala Leu Ala Ile Glu Arg Glu
    290                 295                 300

Leu Val Pro Glu Ala Glu Gln Ser His Leu Val Glu Thr Met Glu Glu
305                 310                 315                 320

Ile Met Leu Ala His Pro Glu Asn Trp Gln Lys Tyr Tyr Arg Gly Ser
                325                 330                 335

Ala Glu Gln Gln Arg Leu Leu Arg Val Tyr Ser Tyr Ser Asp Arg Ile
            340                 345                 350

Arg Tyr Tyr Trp Gly Arg Pro Glu Ala Glu Ala Val Thr Arg Leu
    355                 360                 365

Met Arg Asn Leu His Gln Thr Thr Ile Pro Glu Thr Leu Leu Ser Gln
370                 375                 380

Tyr Cys Pro Arg Glu Tyr Glu Ala Met Arg Glu Gly Arg Leu Arg Asn
385                 390                 395                 400

Asp Pro Ala Glu Leu Thr Ile Ala Ser Ile Arg Thr Val Leu Glu Ser
                405                 410                 415

Tyr Ser Ser Ala Cys Arg Gly Asp Gly Ser Asn Ser Gly Lys Gln
            420                 425                 430

<210> SEQ ID NO 4
<211> LENGTH: 1296
<212> TYPE: DNA
<213> ORGANISM: Artificial Sequence
<220> FEATURE:
<223> OTHER INFORMATION: DNA sequence of Tagatose-biphosphate aldolase,
      CJ_AB_F4E derived from Acidobacteriales bacterium

<400> SEQUENCE: 4
atgtccgaca atttgcaggt gtttcttcgt gagtcccgag gccggcgcgg catctattcg      60
gtatgctccg cgcatccccg ggtgatcgag gccgccatgc ggcaagctgg cgcagacggc     120
acgcatctgc tgctggaagc gacgtcgaat caggtgaacc aagccggagg ctacaccggc     180
atgactcccg cgatgtttcg cgattacgtt tatgacattg cacaggagat cggcttcgac     240

```
cgcagccgtt tgattcttgg cggagatcat ttgggcccca atccctggca gcagctcgac    300
gccagcacag cgatgcagta tgcagaggag atggttcgac tgtacatcga ggcaggattc    360
accaagattc atctcgacgc cagcatgcgt tgtgccgacg atgcggcaat cgttcccgat    420
gaagtgatgg caggacgcgc cgccgcattg tgcagcgcgg ctgagtcggc gcgagcacgg    480
ctgggactgg cgccggtggt ctacgtgatc ggaaccgagg ttccaacgcc gggtggagca    540
agccatgctc tcaacacgct ggaggtaaca acgcgggagg cagtcgagca tacgctgtcg    600
gttcatcgca aagccttcca cgatgcggga ttggacgctg catggcagcg cgtgatcgcg    660
gtggtcgtgc agccgggcgt ggagttcgat cacgatagcg ttgtcgacta tgacgccgca    720
aaagcgggcc atttgcaaga atttctacaa gcccacccgg aactggtgat ggaggcacac    780
tccagcgatt accagaagcc gcaagcctac aaggaactgg tccgtgatgg cttcgcgatc    840
ctgaaggtcg ggcctgcgtt gacgtttgcg ctgcgggaga tgctctacgc gctggccgcc    900
atcgagcggg aactggtgcc ggaggcggag cagtcccatc tggtagagac gatggaagag    960
atcatgctgg ctcatcccga aactggcagg aagtactatc gcggaagcgc agagcagcag   1020
cgattgctgc gcgtctatag ctacagcgac cgcattcgct attactgggg acgtccggag   1080
gccgaagctg ccgtcacgcg cctgatgcga aatctgcatc agacgacgat cccgagact    1140
ctcctaagcc agtattgtcc gcgcgaatat gaggcaatgc gcgaaggaag actgcgaaac   1200
gatccggctg agttgacgat cgcgagcatt cgaactgtgc tggagtccta cagcagcgct   1260
tgtcgcggtg acggctcgaa ctccggtaaa cagtaa                             1296
```

<210> SEQ ID NO 5
<211> LENGTH: 435
<212> TYPE: PRT
<213> ORGANISM: Artificial Sequence
<220> FEATURE:
<223> OTHER INFORMATION: An amino acid sequence of Tagatose-biphosphate
     aldolase, CJ_KO_F4E derived from Kosmotoga olearia

<400> SEQUENCE: 5

Met Lys Lys His Pro Leu Gln Asp Ile Val Ser Leu Gln Lys Gln Gly
1               5                   10                  15

Ile Pro Lys Gly Val Phe Ser Val Cys Ser Ala Asn Arg Phe Val Ile
            20                  25                  30

Glu Thr Thr Leu Glu Tyr Ala Lys Met Lys Gly Thr Thr Val Leu Ile
        35                  40                  45

Glu Ala Thr Cys Asn Gln Val Asn Gln Phe Gly Gly Tyr Thr Gly Met
    50                  55                  60

Thr Pro Ala Asp Phe Arg Glu Met Val Phe Ser Ile Ala Glu Asp Ile
65                  70                  75                  80

Gly Leu Pro Lys Asn Lys Ile Ile Leu Gly Gly Asp His Leu Gly Pro
                85                  90                  95

Asn Pro Trp Lys Gly Gln Pro Ser Asp Gln Ala Met Arg Asn Ala Ile
            100                 105                 110

Glu Met Ile Arg Glu Tyr Ala Lys Ala Gly Phe Thr Lys Leu His Leu
        115                 120                 125

Asp Ala Ser Met Arg Leu Ala Asp Asp Pro Gly Asn Glu Asn Glu Pro
    130                 135                 140

Leu Asn Pro Glu Val Ile Ala Glu Arg Thr Ala Leu Leu Cys Leu Glu
145                 150                 155                 160

Ala Glu Arg Ala Phe Lys Glu Ser Ala Gly Ser Leu Arg Pro Val Tyr
                165                 170                 175

Val Ile Gly Thr Asp Val Pro Pro Gly Gly Ala Gln Asn Glu Gly
            180                 185                 190

Lys Ser Ile His Val Thr Ser Val Gln Asp Phe Glu Arg Thr Val Glu
            195                 200                 205

Leu Thr Lys Lys Ala Phe Phe Asp His Gly Leu Tyr Glu Ala Trp Gly
210                 215                 220

Arg Val Ile Ala Val Val Gln Pro Gly Val Glu Phe Gly Asn Glu
225                 230                 235                 240

His Ile Phe Glu Tyr Asp Arg Asn Arg Ala Arg Glu Leu Thr Glu Ala
                245                 250                 255

Ile Lys Lys His Pro Asn Ile Val Phe Glu Gly His Ser Thr Asp Tyr
            260                 265                 270

Gln Thr Ala Lys Ala Leu Lys Glu Met Val Glu Asp Gly Val Ala Ile
            275                 280                 285

Leu Lys Val Gly Pro Ala Leu Thr Phe Ala Leu Arg Glu Ala Phe Phe
290                 295                 300

Ala Leu Ser Ser Ile Glu Lys Glu Leu Phe Tyr Asp Thr Pro Gly Leu
305                 310                 315                 320

Cys Ser Asn Phe Val Glu Val Val Glu Arg Ala Met Leu Asp Asn Pro
                325                 330                 335

Lys His Trp Glu Lys Tyr Tyr Gln Gly Glu Glu Arg Glu Asn Arg Leu
            340                 345                 350

Ala Arg Lys Tyr Ser Phe Leu Asp Arg Leu Arg Tyr Tyr Trp Asn Leu
            355                 360                 365

Pro Glu Val Arg Thr Ala Val Asn Lys Leu Ile Thr Asn Leu Glu Thr
370                 375                 380

Lys Glu Ile Pro Leu Thr Leu Ile Ser Gln Phe Met Pro Met Gln Tyr
385                 390                 395                 400

Gln Lys Ile Arg Asn Gly Leu Leu Arg Lys Asp Pro Ile Ser Leu Ile
                405                 410                 415

Lys Asp Arg Ile Thr Leu Val Leu Asp Asp Tyr Tyr Phe Ala Thr His
            420                 425                 430

Pro Glu Cys
        435

<210> SEQ ID NO 6
<211> LENGTH: 1308
<212> TYPE: DNA
<213> ORGANISM: Artificial Sequence
<220> FEATURE:
<223> OTHER INFORMATION: DNA sequence of Tagatose-biphosphate aldolase,
      CJ_KO_F4E derived from Kosmotoga olearia

<400> SEQUENCE: 6
atgaaaaaac atcctcttca ggacattgtt tcattgcaaa aacagggaat acccaaaggg     60
gttttctctg tatgtagtgc aatagattt gttattgaaa ccactctgga atatgcgaag    120
atgaaaggga caacggttct tatagaggcc acctgcaatc aggtaaacca gttcggtggc    180
tacaccggta tgactcctgc tgatttcaga gaaatggttt tttctatcgc tgaggatatt    240
ggacttccca aaaataaaat catccttggt ggcgaccatc ttggcccaaa tccctggaag    300
ggtcagccgt cagatcaggc tatgcgtaac gccattgaaa tgattcgaga atacgctaaa    360
gctgggttta ccaagcttca tctggatgcc agcatgcgtc ttgcagacga tccggggaac    420
gaaaacgagc cgctgaaccc ggaagttata gcggaaagaa cagctcttct ctgtcttgaa    480

```
gccgagaggg cttttaaaga atccgccggt tctctccggc ctgtttacgt tattggtacg    540
gatgttccgc caccgggtgg agcgcaaaac gaaggtaaat cgattcatgt aaccagtgtt    600
caggattttg agcgtaccgt tgagttgacc aaaaaggcat ttttcgacca tggtttgtat    660
gaagcctggg aagggtgat tgcggttgtt gtgcaaccgg gagtagaatt cgggaatgaa     720
catatattcg aatatgatag aaatcgagcg agagaactta ctgaggcgat aaaaaagcat    780
ccaaatatag tttttgaagg tcactcgaca gattatcaaa cggcaaaagc attgaaagaa    840
atggtagaag acggtgtagc catactcaag gttgggccag ctctaacatt tgcgctcaga    900
gaggcttttt ttgcgttgag cagcattgaa aaagagttat tttatgatac acccgggctt    960
tgttcaaact ttgttgaagt tgtcgagaga gcgatgcttg acaatccaaa acattgggaa   1020
aaatattacc agggagaaga gagagaaaat agattagccc gtaaatacag ctttctcgat   1080
cgcttgaggt attactggaa tcttcctgag gttagaacag cggtgaataa gctgataacc   1140
aaccttgaaa caaagaaat cccgttaacg cttataagcc agttcatgcc gatgcagtac    1200
caaaaaatca gaaacggttt gctaagaaag gatccaataa gccttataaa agatcgaatt   1260
acccttgttc ttgatgacta ctatttcgca actcaccctg aatgttga                1308
```

```
<210> SEQ ID NO 7
<211> LENGTH: 420
<212> TYPE: PRT
<213> ORGANISM: Artificial Sequence
<220> FEATURE:
<223> OTHER INFORMATION: An amino acid sequence of Tagatose-biphosphate
      aldolase, CJ_RP_F4E derived from Rhodothermus profundi

<400> SEQUENCE: 7

Met Gln Ala His Val Leu Leu Ala Pro Ser Phe Glu Gln Leu Ala Asp
1               5                   10                  15

His Arg His Gly Phe Val Gly Trp Leu Val Asp Leu Leu Arg Gly Pro
            20                  25                  30

Leu Ala Tyr Arg His Thr Leu Leu Ala Val Cys Pro Asn Ser Glu Ala
        35                  40                  45

Val Thr Arg Ala Ala Leu Glu Ala Ala Arg Glu Ala Asn Ala Pro Leu
    50                  55                  60

Phe Phe Ala Ala Thr Leu Asn Gln Val Asp Leu Asp Gly Gly Tyr Thr
65                  70                  75                  80

Gly Trp Thr Pro Ala Thr Leu Ala Arg Phe Val Ala Asp Glu Arg Ile
                85                  90                  95

Arg Leu Gly Leu Arg Ala Pro Val Val Leu Gly Leu Asp His Gly Gly
            100                 105                 110

Pro Trp Lys Lys Asp Trp His Val Arg Asn Arg Leu Pro Tyr Glu Ala
        115                 120                 125

Thr Leu Gln Ala Val Leu Arg Ala Ile Glu Ala Cys Leu Asp Ala Gly
    130                 135                 140

Tyr Gly Leu Leu His Leu Asp Pro Thr Val Asp Leu Glu Leu Pro Pro
145                 150                 155                 160

Gly Thr Pro Val Pro Ile Pro Arg Ile Val Glu Arg Thr Val Ala Leu
                165                 170                 175

Leu Gln His Ala Glu Thr Tyr Arg Gln Gln Arg Arg Leu Pro Pro Val
            180                 185                 190

Ala Tyr Glu Val Gly Thr Glu Glu Val Gly Gly Gly Leu Gln Ala Glu
        195                 200                 205
```

Ala Arg Met Ala Glu Phe Leu Asp Arg Leu Trp Thr Val Leu Asp Arg
    210                 215                 220

Glu Gly Leu Pro Arg Pro Val Phe Val Val Gly Asp Ile Gly Thr Arg
225                 230                 235                 240

Leu Asp Thr His Thr Phe Asp Phe Glu Arg Ala Arg Arg Leu Asp Ala
                245                 250                 255

Leu Val Arg Arg Tyr Gly Ala Leu Ile Lys Gly His Tyr Thr Asp Gly
            260                 265                 270

Val Asp Arg Leu Asp Leu Tyr Pro Gln Ala Gly Ile Gly Gly Ala Asn
        275                 280                 285

Val Gly Pro Gly Leu Ala Ala Ile Glu Phe Glu Ala Leu Glu Ala Leu
290                 295                 300

Val Ala Glu Ala His Arg Arg Lys Leu Pro Val Thr Phe Asp Arg Thr
305                 310                 315                 320

Ile Arg Gln Ala Val Ile Glu Ser Gly Arg Trp Gln Lys Trp Leu Arg
                325                 330                 335

Pro Glu Glu Lys Gly Arg Pro Phe Glu Ala Leu Pro Pro Glu Arg Gln
            340                 345                 350

Arg Trp Leu Val Ala Thr Gly Ser Arg Tyr Val Trp Thr His Pro Ala
        355                 360                 365

Val Arg Gln Ala Arg His Gln Leu Tyr Gln Val Leu Ala Pro Trp Leu
    370                 375                 380

Asp Ala Asp Ala Phe Val Arg Ala Arg Ile Lys Ala Arg Leu Met Asp
385                 390                 395                 400

Tyr Phe Arg Ala Phe Asn Leu Ile Gly Phe Asn Glu Arg Leu Gln Ala
                405                 410                 415

Phe Leu Pro Asn
            420

<210> SEQ ID NO 8
<211> LENGTH: 1263
<212> TYPE: DNA
<213> ORGANISM: Artificial Sequence
<220> FEATURE:
<223> OTHER INFORMATION: DNA sequence of Tagatose-biphosphate aldolase,
      CJ_RP_F4E derived from Rhodothermus profundi

<400> SEQUENCE: 8
atgcaggcgc acgtcctgct tgccccttcg ttcgagcagc tagcagacca caggcacgga    60
tttgttggct ggttggtcga tttgctgcgc ggaccgctgg cttaccggca cacgctgctg   120
gccgtatgtc ccaattccga agccgtaacg cgcgccgccc tggaagctgc gcgcgaagcc   180
aacgccccgc tattttttgc ggctaccctg aaccaggtcg acctggatgg cggatatacc   240
ggctggaccc cggccacgct ggctcgtttt gttgccgacg agcgcatccg cctgggcctt   300
cgcgcccctg tcgtacttgg tctggatcac ggtggcccct ggaaaaagga ttggcatgtc   360
cgcaaccgtc ttccgtacga ggcaacgctc caggcggtgc ttcgcgcgat tgaggcctgc   420
ctcgacgcag gttatgggct gcttcatctg gacccgacgg tagatctgga attgccgccc   480
ggcacacccg tccccatccc acgtattgtc gaacgaacgg tagcgctttt acaacatgct   540
gaaacgtatc gccaacagcg tcgcctgccc ccggtcgcct acgaggtagg cacggaggag   600
gttggcggcg gcctgcaggc tgaggcgcga atgcagaatt tctggatcg actctggacc   660 gtcctggatc gggaagggct accccgtccg gtgtttgtgg tgggtgacat tggcaccccgg   720 cttgacacgc acaccttcga ctttgaacgc gcccgtcgcc tggatgccct ggtgcgccgc   780

```
tacggtgccc tgatcaaggg gcactacacc gatggagtag accgcctgga tctatatcca    840
caggcgggta tcggtggagc aaacgtgggg cctggcctgg ctgctatcga gtttgaagcg    900
ctggaggccc tggtggccga agcgcaccgc cgcaagctgc ccgttacctt tgaccggacc    960
atccgccagg ctgtcattga agtggacgc tggcaaaaat ggctgcgccc tgaagagaaa   1020
ggacgtccct ttgaagcatt acctccagaa cgccagcggt ggctggtcgc tacaggcagc   1080
cgctacgtgt ggacgcaccc ggctgtccgg caggcgcgcc atcaattgta tcaggtgctc   1140
gctccctggc tcgatgccga tgcttttgtg cgcgcgcgca tcaaggcccg cctgatggac   1200
tacttccgcg ctttcaacct gataggcttc aatgaacggc tgcaggcctt tttacctaat   1260
tga                                                                1263
```

<210> SEQ ID NO 9
<211> LENGTH: 420
<212> TYPE: PRT
<213> ORGANISM: Artificial Sequence
<220> FEATURE:
<223> OTHER INFORMATION: An amino acid sequence of Tagatose-biphosphate
      aldolase, CJ_RM_F4E derived from Rhodothermus marinus

<400> SEQUENCE: 9

```
Met Gln Ala Gln Ala Leu Leu Thr Val Pro Phe Asp Arg Val Ala Thr
1               5                   10                  15

His Ala Arg Gly Phe Val Gly Trp Val Ala Glu Leu Leu Gln Gly Pro
            20                  25                  30

Leu Ala Tyr Gln His Thr Leu Leu Ala Val Cys Pro Asn Ser Glu Ala
        35                  40                  45

Val Thr Arg Ala Ala Leu Glu Ala Ala Glu Ala Asn Ala Pro Leu
    50                  55                  60

Leu Phe Ala Ala Thr Leu Asn Gln Val Asp Leu Asp Gly Gly Tyr Thr
65                  70                  75                  80

Gly Trp Thr Pro Ala Thr Leu Ala Arg Phe Val Ala Asp Glu Leu Ala
                85                  90                  95

Arg Leu Asp Leu His Ile Pro Val Val Leu Gly Leu Asp His Gly Gly
            100                 105                 110

Pro Trp Lys Lys Asp Leu His Ala Arg Asn Arg Leu Ser Phe Glu Glu
        115                 120                 125

Thr Phe Gln Ala Val Leu Arg Ala Ile Glu Ala Cys Leu Asp Ala Gly
    130                 135                 140

Tyr Gly Leu Leu His Leu Asp Pro Thr Val Asp Leu Glu Leu Ser Pro
145                 150                 155                 160

Gly Thr Pro Val Pro Ile Pro Arg Ile Val Glu Arg Ser Val Ala Leu
                165                 170                 175

Leu Arg His Ala Glu Thr Tyr Arg Leu Arg Arg Asn Leu Pro Pro Val
            180                 185                 190

Ala Tyr Glu Val Gly Thr Glu Glu Val Gly Gly Leu Gln Ala Glu
        195                 200                 205

Ala Arg Met Ala Glu Phe Leu Asp Arg Leu Trp Thr Ala Leu Asp Arg
    210                 215                 220

Glu Gly Leu Pro His Pro Val Phe Val Gly Asp Ile Gly Thr Arg
225                 230                 235                 240

Leu Asp Thr Arg Thr Phe Asp Phe Glu Arg Ala Arg Arg Leu Asp Ala
                245                 250                 255
```

```
Leu Val Arg Arg Tyr Gly Ala Leu Ile Lys Gly His Tyr Thr Asp Asp
              260                 265                 270

Val Asp Arg Leu Asp Leu Tyr Pro Lys Ala Gly Ile Gly Gly Ala Asn
          275                 280                 285

Val Gly Pro Gly Leu Ala Ala Ile Glu Phe Glu Ala Leu Glu Ala Leu
      290                 295                 300

Val Glu Glu Ala Arg Arg Gly Leu Ser Val Thr Phe Asp Gln Ala
305                 310                 315                 320

Ile Arg Arg Ala Val Val Glu Ser Gly Arg Trp Thr Lys Trp Leu Gln
                  325                 330                 335

Pro Glu Glu Lys Gly Gln Pro Phe Asp Ala Leu Asp Pro Glu Arg Gln
              340                 345                 350

Arg Trp Leu Val Ala Thr Gly Ser Arg Tyr Val Trp Thr His Pro Ala
          355                 360                 365

Val Leu Gln Ala Arg Arg Glu Leu Tyr Glu Ala Leu Ala Pro Trp Leu
      370                 375                 380

Asp Ala Asp Ala Phe Val Arg Thr Arg Ile Lys Ala Arg Leu Met Asp
385                 390                 395                 400

Tyr Phe Arg Ala Phe Asn Leu Ile His Phe Asn Glu Arg Leu Gln Ala
                  405                 410                 415

Phe Leu Pro Glu
          420

<210> SEQ ID NO 10
<211> LENGTH: 1263
<212> TYPE: DNA
<213> ORGANISM: Artificial Sequence
<220> FEATURE:
<223> OTHER INFORMATION: DNA sequence of Tagatose-biphosphate aldolase,
      CJ_RM_F4E derived from Rhodothermus marinus

<400> SEQUENCE: 10
atgcaggcgc aggccctgct gaccgttcca tttgatcggg tggcgaccca cgcacgcggg     60
tttgtgggct gggtggccga actgctgcag gggcccctgg cctatcagca tacgctgctg    120
gctgtctgtc ccaattcgga agcggtaaca cgggccgcgc tggaggccgc cgccgaggcc    180
aacgccccgc tgcttttgc cgccacgctg aaccaggtgg acctcgacgg cggctacacc    240
ggctggacgc ccgccacgct ggcccggttc gtggcggacg aactggcccg cctggacctg    300
cacatccccg tcgtgctcgg cctggaccac ggcggcccct ggaaaaagga tctgcacgcc    360
cgcaaccgat tgtcctttga gaaaccttc caggccgtgc tgcgggccat cgaggcctgt    420
ctggatgccg gctacggcct gctgcacctg gatccgacgg tcgatctgga gctatcgccc    480
ggcacgccgg tgcccatccc cgcattgtc gaacgctcgg tagcgctttt gcgtcatgcc    540
gaaacctatc gacttcgacg taacctgccg ccggtcgcct acgaggtggg caccgaagaa    600
gtcggcggcg cctgcaggc cgaagcgcgc atggcggagt ttctggatcg cctctggacc    660
gcactggacc gggaaggcct gccccatcca gtcttcgtgg tgggcgacat cggcacccgg    720
ctcgacacgc gcacgttcga cttcgagcgg gcccgacggc tggacgcgct ggtgcgccgc    780
tacggtgccc tcatcaaagg gcactacacc gacgacgtga tcgcctcga tctgtacccg    840 aaggcgggca tcggcggggc caacgtgggc ccgggcctgg ccgccatcga gtttgaagcg    900
ctggaggcgc tggtggagga gcccgtcgc gcggtctttc ggtgacgtt cgatcaggcc    960 atccgccggg ccgtcgtcga aagcggacgc tggacgaagt ggctccaacc ggaagagaaa   1020
```

```
ggccagccgt tcgatgcgct ggatcccgag cggcaacgct ggctggtggc caccggcagc      1080
cgctacgtgt ggacgcatcc ggccgtcctg caggcccgcc gcgaactcta cgaggcgctc      1140 gcccctggc tcgatgccga cgctttcgtg cgcacgcgca tcaaagcacg cctgatggac       1200
tactttcgtg ccttcaacct gatccatttc aacgagcggc tgcaggcctt ctctccccgaa    1260 tga                                                                   1263
```

<210> SEQ ID NO 11
<211> LENGTH: 448
<212> TYPE: PRT
<213> ORGANISM: Artificial Sequence
<220> FEATURE:
<223> OTHER INFORMATION: An amino acid sequence of Tagatose-biphosphate
      aldolase, CJ_LP_F4E derived from Limnochorda pilosa

<400> SEQUENCE: 11

```
Met Gln Thr Ser Thr Ala Tyr Val Arg Gln Val Ile Trp Gly Gln Gly
1               5                   10                  15

Thr Arg Asp Pro Arg Gly Ile Tyr Ser Val Cys Thr Ala Asp Pro Leu
            20                  25                  30

Val Leu Arg Ala Ala Leu Lys Gln Ala Val Glu Asp Gly Ser Pro Ala
        35                  40                  45

Leu Ile Glu Ala Thr Ser Asn Gln Val Asn Gln Phe Gly Gly Tyr Thr
    50                  55                  60

Gly Met Glu Pro Pro Ala Phe Val Glu Phe Val Leu Gly Leu Ala Arg
65                  70                  75                  80

Glu Met Gly Leu Pro Pro Glu Arg Leu Ile Leu Gly Gly Asp His Leu
                85                  90                  95

Gly Pro Asn Pro Trp Gln Arg Leu Ala Ala Glu Ala Met Arg His
            100                 105                 110

Ala Cys Asp Leu Val Glu Ala Phe Val Ala Cys Gly Phe Thr Lys Ile
        115                 120                 125

His Leu Asp Ala Ser Met Pro Leu Gly Glu Glu Arg Ala Gly Gly Ala
    130                 135                 140

Leu Ser Lys Arg Val Val Ala Glu Arg Thr Ala Gln Leu Cys Glu Ala
145                 150                 155                 160

Ala Glu Ala Ala Phe Arg Lys Arg Ser Gln Ala Glu Gly Ala Ser Ala
                165                 170                 175

Pro Pro Leu Tyr Val Ile Gly Ser Asp Val Pro Pro Gly Gly Glu
        180                 185                 190

Thr Ser Gly Ser Gln Gly Pro Lys Val Thr Thr Pro Glu Glu Phe Glu
    195                 200                 205

Glu Thr Val Ala Leu Thr Arg Ala Thr Phe His Asp Arg Gly Leu Asp
210                 215                 220

Asp Ala Trp Gly Arg Val Ile Ala Val Val Gln Pro Gly Val Asp
225                 230                 235                 240

Phe Gly Glu Trp Gln Val His Pro Tyr Asp Arg Ala Ala Ala Ser
                245                 250                 255

Leu Thr Arg Ala Leu Thr Gln His Pro Gly Leu Ala Phe Glu Gly His
        260                 265                 270

Ser Thr Asp Tyr Gln Thr Pro Gly Arg Leu Arg Gln Met Ala Glu Asp
    275                 280                 285

Gly Ile Ala Ile Leu Lys Val Gly Pro Ala Leu Thr Phe Ala Lys Arg
290                 295                 300
```

Glu Ala Leu Phe Ala Leu Asn Ala Leu Glu Ser Glu Val Leu Gly Thr
305                 310                 315                 320

Asp Gly Arg Ala Arg Arg Ser Asn Val Glu Ala Ala Leu Glu Glu Ala
            325                 330                 335

Met Leu Ala Asp Pro Arg His Trp Ser Ala Tyr Tyr Ser Gly Asp Glu
        340                 345                 350

His Glu Leu Arg Leu Lys Arg Lys Tyr Gly Leu Ser Asp Arg Cys Arg
    355                 360                 365

Tyr Tyr Trp Pro Val Pro Ser Val Gln Glu Ala Val Gln Arg Leu Leu
370                 375                 380

Gly Asn Leu Arg Glu Ala Gly Ile Pro Leu Pro Leu Leu Ser Gln Phe
385                 390                 395                 400

Leu Pro Arg Gln Tyr Glu Arg Val Arg Glu Gly Val Leu Arg Asn Asp
                405                 410                 415

Pro Glu Glu Leu Val Leu Asp Arg Ile Arg Asp Val Leu Arg Gly Tyr
            420                 425                 430

Ala Ala Ala Val Gly Thr Gly Ala Arg Arg Ala Glu Pro Ser Pro Ala
        435                 440                 445

<210> SEQ ID NO 12
<211> LENGTH: 1347
<212> TYPE: DNA
<213> ORGANISM: Artificial Sequence
<220> FEATURE:
<223> OTHER INFORMATION: DNA sequence of Tagatose-biphosphate aldolase,
      CJ_LP_F4E derived from Limnochorda pilosa

<400> SEQUENCE: 12

```
atgcaaacct cgacggcgta cgtgaggcag gtcatttggg gtcaagggac gagggacccc    60
cgcggcatct actcggtctg taccgcagac ccctcgtcc ttcgggccgc cctcaagcag    120
gcggtggagg atggctcccc cgcgctgatc gaggcgacgt ccaaccaggt gaaccagttc    180
ggcgggtata cggggatgga gccccggcg ttcgtggagt tcgtgctggg acttgcccgc    240
gagatgggac tcccgcccga gcggctgatc ctcggggcg atcacctcgg ccccaaccca    300
tggcagcggc tggcggccga agaggccatg cggcatgcct cgacctcgt cgaggccttc    360 gtggcctgcg gcttcaccaa gattcacctg gacgccagca tgcccctggg ggaggaacgg    420
gcaggcggtg cgctttcgaa acgggtggtg ccgaacgga ccgcccagct ctgcgaggcg    480
gccgaggcgg ccttcaggaa gcggtcccag gcggaggggg cgtcggcgcc tccgctctac    540
gtcatcggct ccgacgtgcc tccgcccggc ggcgagacct ccgggagcca ggggcccaag    600
gtgaccacgc cggaggagtt cgaggagacg tcgcgctga gcgggcgac ctttcacgat    660 cggggcctgg acgacgcctg ggacggggtg atcgccgtgg tggtccagcc gggggtggac    720
ttcggcgagt ggcaggttca ccctacgat cgggccgccg cggcgagcct acccgagcc    780 ttgacgcagc atccggggct ggccttcgaa gggcactcca ccgactacca gacgccgggg    840
cggcttcgcc agatggcgga agacggcatc gccatcctga aggtggggcc ggccctcacc    900
ttcgccaagc gggaagcgct cttcgcccctg aacgccctgg agtccgaagt gctggggacg    960
gacggccgag cacggcgctc caactgcgaa gccgccctcg aagaggcgat gctcgccgat    1020
ccccgtcact ggagcgccta ctacagcggg gacgagcacg agctccgtct caagcggaag    1080
tacgccctct ccgaccggtg tcgctactac tggcccgtcc cttcggtgca ggaggccgtc    1140
cagcgcctcc ttggcaacct gcgcgaggcg gggatcccct gcccctgct gagccagttc    1200
```

```
ctgccgcgcc agtacgagcg ggtgcgggag ggcgtcctgc gcaacgaccc ggaggagctg    1260
gtcctggacc ggattcgtga cgtgttgcgg ggatatgcgg cggccgtggg gacgggcgct    1320
aggcgggcgg agccatcacc cgcgtga                                         1347
```

<210> SEQ ID NO 13
<211> LENGTH: 453
<212> TYPE: PRT
<213> ORGANISM: Artificial Sequence
<220> FEATURE:
<223> OTHER INFORMATION: An amino acid sequence of Tagatose-biphosphate aldolase, CJ_Cab_F4E derived from Caldithrix abyssi

<400> SEQUENCE: 13

```
Met Ser Leu His Pro Leu Asn Lys Leu Ile Glu Arg His Lys Lys Gly
1               5                   10                  15

Thr Pro Val Gly Ile Tyr Ser Val Cys Ser Ala Asn Pro Phe Val Leu
            20                  25                  30

Lys Ala Ala Met Leu Gln Ala Gln Lys Asp Gln Ser Leu Leu Leu Ile
        35                  40                  45

Glu Ala Thr Ser Asn Gln Val Asp Gln Phe Gly Gly Tyr Thr Gly Met
    50                  55                  60

Arg Pro Glu Asp Phe Lys Thr Met Thr Leu Glu Leu Ala Ala Glu Asn
65                  70                  75                  80

Asn Tyr Asp Pro Gln Gly Leu Ile Leu Gly Gly Asp His Leu Gly Pro
                85                  90                  95

Asn Arg Trp Thr Lys Leu Ser Ala Ser Arg Ala Met Asp Tyr Ala Arg
            100                 105                 110

Glu Gln Ile Ala Ala Tyr Val Lys Ala Gly Phe Ser Lys Ile His Leu
        115                 120                 125

Asp Ala Thr Met Pro Leu Gln Asn Asp Ala Thr Asp Ser Ala Gly Arg
    130                 135                 140

Leu Pro Val Glu Thr Ile Ala Gln Arg Thr Ala Glu Leu Cys Ala Val
145                 150                 155                 160

Ala Glu Gln Thr Tyr Arg Gln Ser Asp Gln Leu Phe Pro Pro Val
                165                 170                 175

Tyr Ile Val Gly Ser Asp Val Pro Ile Pro Gly Gly Ala Gln Glu Ala
            180                 185                 190

Leu Asn Gln Ile His Ile Thr Glu Val Lys Glu Val Gln Gln Thr Ile
        195                 200                 205

Asp His Val Arg Arg Ala Phe Glu Lys Asn Gly Leu Glu Ala Ala Tyr
    210                 215                 220

Glu Arg Val Cys Ala Val Val Gln Pro Gly Val Glu Phe Ala Asp
225                 230                 235                 240

Gln Ile Val Phe Glu Tyr Ala Pro Asp Arg Ala Ala Leu Lys Asp
                245                 250                 255

Phe Ile Glu Ser His Ser Gln Leu Val Tyr Glu Ala His Ser Thr Asp
            260                 265                 270

Tyr Gln Thr Ala Pro Leu Leu Arg Gln Met Val Lys Asp His Phe Ala
        275                 280                 285

Ile Leu Lys Val Gly Pro Ala Leu Thr Phe Ala Leu Arg Glu Ala Ile
    290                 295                 300

Phe Ala Leu Ala Phe Met Glu Lys Glu Leu Leu Pro Leu His Arg Ala
305                 310                 315                 320

Leu Lys Pro Ser Ala Ile Leu Glu Thr Leu Asp Gln Thr Met Asp Lys
                325                 330                 335
```

```
Asn Pro Ala Tyr Trp Gln Lys His Tyr Gly Gly Thr Lys Glu Glu Val
                340                 345                 350

Arg Phe Ala Gln Arg Phe Ser Leu Ser Asp Arg Ile Arg Tyr Tyr Trp
            355                 360                 365

Pro Phe Pro Lys Val Gln Lys Ala Leu Arg Gln Leu Leu Lys Asn Leu
370                 375                 380

Gln Gln Ile Ser Ile Pro Leu Thr Leu Val Ser Gln Phe Met Pro Glu
385                 390                 395                 400

Glu Tyr Gln Arg Ile Arg Gln Gly Thr Leu Thr Asn Asp Pro Gln Ala
                405                 410                 415

Leu Ile Leu Asn Lys Ile Gln Ser Val Leu Lys Gln Tyr Ala Glu Ala
                420                 425                 430

Thr Gln Ile Gln Asn Ser Leu Thr Phe Thr Gln Asn Gln Asn Ser Leu
            435                 440                 445

Ala Met Glu Arg Leu
    450
```

<210> SEQ ID NO 14
<211> LENGTH: 1362
<212> TYPE: DNA
<213> ORGANISM: Artificial Sequence
<220> FEATURE:
<223> OTHER INFORMATION: DNA sequence of Tagatose-biphosphate aldolase, CJ_Cab_F4E derived from Caldithrix abyssi

<400> SEQUENCE: 14

```
atgagtctgc atcctttaaa taaattaatc gagcgacaca aaaaaggaac gccggtcggt      60
atttattccg tctgttcggc caatcccttt gttttgaaag cggccatgct acaggcgcaa     120
aaggatcagt ctttgctact tattgaggcc acttccaacc aggtagatca attcggcggt     180
tacaccggca tgcggcccga agattttaaa acaatgacgc ttgaactggc agccgaaaac     240
aattacgatc cacagggatt aatcctgggc ggcgaccatc tggggcccaa ccgctggaca     300
aaactgagcg cctcccgggc catggactac gccagagagc agattgccgc ttatgttaaa     360
gccggctttt ccaaaatcca cttagacgcc accatgccct tgcaaaacga tgccacagat     420
tccgccggcc gccttccagt cgaaacaatc gctcaacgta ccgcagaatt atgcgccgtg     480
gccgaacaaa cttaccggca gagcgaccaa ctctttccgc cgcctgttta cattgtcggc     540
agcgacgtgc ccatcccggg cggcgcgcaa gaagcgctga accagatcca tattacggag     600
gtaaaagagg ttcaacagac cattgatcac gtgcggcggg cctttgaaaa aaacggcctg     660
gaagcggctt acgaaagagt ttgcgccgtt gtcgtgcagc caggcgttga attcgccgat     720
caaatcgttt ttgaatacgc tcccgacaga gcggcggcct aaaagatttt attgaaagc     780
cattcgcagc tggtttatga agcgcactct actgattacc agaccgcacc tcttttgcgc     840
cagatggtaa aagatcactt tgccatttta aaggtcgggc ctgcgctcac ctttgccctg     900
cgcgaagcca ttttgctct ggcctttatg gaaaagagc ttttgccatt gcacagagcg     960
ctcaaacctt ctgccattct ggaaacgctg accaaacga tggacaaaaa ccctgcttac    1020
tggcaaaagc attacggcgg aacaaaggaa gaagtacgct ttgcgcagcg gtttagcctg    1080
agcgaccgca ttcgttacta ctggccgttt ccaaaggttc aaaaggccct gcgccaattg    1140
ctaaaaaact tgcaacaaat ttccattcct ctaactttgg taagccagtt catgccagag    1200
gaataccaac gtattcgcca aggaacgtta accaacgatc cgcaggcgct gatttttgaac    1260
```

```
aaaattcaaa gcgtattaaa gcaatacgcg gaggcgacgc aaattcaaaa ctctttgaca      1320
ttcacgcaaa atcaaaattc attagcaatg gagcgactat ga                        1362
```

<210> SEQ ID NO 15
<211> LENGTH: 429
<212> TYPE: PRT
<213> ORGANISM: Artificial Sequence
<220> FEATURE:
<223> OTHER INFORMATION: An amino acid sequence of Tagatose-biphosphate aldolase, CJ_Ckr_F4E derived from Caldicellulosiruptor kronotskyensis

<400> SEQUENCE: 15

```
Met Ser Pro Gln Asn Pro Leu Ile Gly Leu Phe Lys Asn Arg Glu Lys
1               5                   10                  15

Glu Phe Lys Gly Ile Ile Ser Val Cys Ser Ser Asn Glu Ile Val Leu
            20                  25                  30

Glu Ala Val Leu Lys Arg Met Lys Asp Thr Asn Leu Pro Ile Ile Ile
        35                  40                  45

Glu Ala Thr Ala Asn Gln Val Asn Gln Phe Gly Gly Tyr Ser Gly Leu
    50                  55                  60

Thr Pro Ser Gln Phe Lys Glu Arg Val Ile Lys Ile Ala Gln Lys Val
65                  70                  75                  80

Asp Phe Pro Leu Glu Arg Ile Ile Leu Gly Gly Asp His Leu Gly Pro
                85                  90                  95

Phe Val Trp Arg Asp Gln Glu Pro Glu Ile Ala Met Glu Tyr Ala Lys
            100                 105                 110

Gln Met Ile Lys Glu Tyr Ile Lys Ala Gly Phe Thr Lys Ile His Ile
        115                 120                 125

Asp Thr Ser Met Pro Leu Lys Gly Glu Asn Ser Ile Asp Asp Glu Ile
    130                 135                 140

Ile Ala Lys Arg Thr Ala Val Leu Cys Arg Ile Ala Glu Glu Cys Phe
145                 150                 155                 160

Glu Lys Ile Ser Ile Asn Asn Pro Tyr Ile Thr Arg Pro Val Tyr Val
                165                 170                 175

Ile Gly Ala Asp Val Pro Pro Gly Gly Glu Ser Ser Ile Cys Gln
            180                 185                 190

Thr Ile Thr Thr Lys Asp Glu Leu Glu Arg Ser Leu Glu Tyr Phe Lys
        195                 200                 205

Glu Ala Phe Lys Lys Glu Gly Ile Glu His Val Phe Asp Tyr Val Val
    210                 215                 220

Ala Val Val Ala Asn Phe Gly Val Glu Phe Gly Ser Asp Glu Ile Val
225                 230                 235                 240

Asp Phe Asp Met Glu Lys Val Lys Pro Leu Lys Glu Leu Leu Ala Lys
                245                 250                 255

Tyr Asn Ile Val Phe Glu Gly His Ser Thr Asp Tyr Gln Thr Lys Glu
            260                 265                 270

Asn Leu Lys Arg Met Val Glu Cys Gly Ile Ala Ile Leu Lys Val Gly
        275                 280                 285

Pro Ala Leu Thr Phe Thr Leu Arg Glu Ala Leu Val Ala Leu Ser His
    290                 295                 300

Ile Glu Glu Glu Ile Tyr Ser Asn Glu Lys Glu Lys Leu Ser Arg Phe
305                 310                 315                 320

Arg Glu Val Leu Leu Asn Thr Met Leu Thr Cys Lys Asp His Trp Ser
                325                 330                 335
```

Lys Tyr Phe Asp Glu Asn Asp Lys Leu Ile Lys Ser Lys Leu Leu Tyr
                340                 345                 350

Ser Tyr Leu Asp Arg Trp Arg Tyr Tyr Phe Glu Asn Glu Ser Val Lys
            355                 360                 365

Ser Ala Val Tyr Ser Leu Ile Gly Asn Leu Glu Asn Val Lys Ile Pro
        370                 375                 380

Pro Trp Leu Val Ser Gln Tyr Phe Pro Ser Gln Tyr Gln Lys Met Arg
385                 390                 395                 400

Lys Lys Asp Leu Lys Asn Gly Ala Ala Asp Leu Ile Leu Asp Lys Ile
                405                 410                 415

Gly Glu Val Ile Asp His Tyr Val Tyr Ala Val Lys Glu
            420                 425

<210> SEQ ID NO 16
<211> LENGTH: 1290
<212> TYPE: DNA
<213> ORGANISM: Artificial Sequence
<220> FEATURE:
<223> OTHER INFORMATION: DNA sequence of Tagatose-biphosphate aldolase,
      CJ_Ckr_F4E derived from Caldicellulosiruptor kronotskyensis

<400> SEQUENCE: 16
atgagtcctc aaaatccatt gattggttta tttaagaata gagaaaaaga gtttaagggt      60
attatttcag tttgttcttc aaatgaaata gtcttagaag cagttttaaa agaatgaaa     120 gatacaaacc taccaattat tattgaagcc acagcgaacc aggtaaatca atttggcggg    180
tattctgggt tgacaccgtc tcagttcaaa aacagagtta taaaaattgc tcaaaaagtt    240
gattttccac ttgagagaat aattcttggt ggggaccatc ttggaccatt tgtgtggcgt    300
gaccaggaac agaaattgc tatggagtat gctaagcaaa tgataaaaga atacataaaa     360
gcaggtttta ccaaaattca catcgacacg agtatgcctt aaaaggggga aacagcata    420 gatgatgaaa taattgctaa agaactgct gtgctctgca ggattgcgga ggagtgtttt    480
gagaagattt ctataaacaa tccctatatt acaaggccag tttatgtgat aggagctgat   540
gtgccacctc ccggcggaga gtcttctatt tgtcaaacaa ttactactaa agatgaatta   600
gaaagaagtt tagaatattt caagaagca tttaaaaagg aaggaattga gcatgtattc    660
gattatgtag ttgctgttgt tgcaaatttt ggagttgaat ttgggagcga tgaaattgtt   720
gattttgata tggaaaaagt aaagccgcta aaagaacttt ggcaaagta caatatagta    780 tttgaaggcc attctacaga ttatcaaaca aagaaaact taaaaagaat ggtcgaatgt    840
ggtattgcaa ttttaaaggt tggtcctgct ctaacattta cattgcgcga agcgttagta   900
gcacttagtc atattgaaga agaaatttat agcaatgaaa aggagaaact gtcaagatt    960 agagaagttt tattgaatac tatgctaaca tgcaaagatc actggagtaa atattttgat  1020
gagaatgata agttaattaa gtcaaagctc ctatatagct atcttgacag atggagatac  1080
tattttgaaa acgagagtgt gaaagtgct gtttattctc ttattggaaa tttagagaat   1140
gttaaaattc caccttggct tgtaagtcag tattttcctt ctcagtacca aagatgaga   1200 aaaaagatt taaaaacgg tgctgccgac ctaatattgg ataaaatagg ggaagtcatt   1260
gaccattatg tttatgcggt aaaagaataa                                    1290

<210> SEQ ID NO 17
<211> LENGTH: 408
<212> TYPE: PRT
<213> ORGANISM: Artificial Sequence
<220> FEATURE:
<223> OTHER INFORMATION: An amino acid sequence of Tagatose-biphosphate aldolase, CJ_CAE_F4E derived from Caldilinea aerophila

<400> SEQUENCE: 17

```
Met Ser Thr Leu Arg His Ile Ile Leu Arg Leu Ile Glu Leu Arg Glu
1               5                   10                  15

Arg Glu Gln Ile His Leu Thr Leu Leu Ala Val Cys Pro Asn Ser Ala
            20                  25                  30

Ala Val Leu Glu Ala Ala Val Lys Val Ala Ala Arg Cys His Thr Pro
        35                  40                  45

Met Leu Phe Ala Ala Thr Leu Asn Gln Val Asp Arg Asp Gly Gly Tyr
    50                  55                  60

Thr Gly Trp Thr Pro Ala Gln Phe Val Ala Glu Met Arg Arg Tyr Ala
65                  70                  75                  80

Val Arg Tyr Gly Cys Thr Thr Pro Leu Tyr Pro Cys Leu Asp His Gly
                85                  90                  95

Gly Pro Trp Leu Lys Asp Arg His Ala Gln Glu Lys Leu Pro Leu Asp
            100                 105                 110

Gln Ala Met His Glu Val Lys Leu Ser Leu Thr Ala Cys Leu Glu Ala
        115                 120                 125

Gly Tyr Ala Leu Leu His Ile Asp Pro Thr Val Asp Arg Thr Leu Pro
    130                 135                 140

Pro Gly Glu Ala Pro Leu Val Pro Ile Val Val Glu Arg Thr Val Glu
145                 150                 155                 160

Leu Ile Glu His Ala Glu Gln Glu Arg Gln Arg Leu Asn Leu Pro Ala
                165                 170                 175

Val Ala Tyr Glu Val Gly Thr Glu Glu Val His Gly Gly Leu Val Asn
            180                 185                 190

Phe Asp Asn Phe Val Ala Phe Leu Asp Leu Leu Lys Ala Arg Leu Glu
        195                 200                 205

Gln Arg Ala Leu Met His Ala Trp Pro Ala Phe Val Val Ala Gln Val
    210                 215                 220

Gly Thr Asp Leu His Thr Thr Tyr Phe Asp Pro Ser Ala Ala Gln Arg
225                 230                 235                 240

Leu Thr Glu Ile Val Arg Pro Thr Gly Ala Leu Leu Lys Gly His Tyr
                245                 250                 255

Thr Asp Trp Val Glu Asn Pro Ala Asp Tyr Pro Arg Val Gly Met Gly
            260                 265                 270

Gly Ala Asn Val Gly Pro Glu Phe Thr Ala Ala Glu Phe Glu Ala Leu
        275                 280                 285

Glu Ala Leu Glu Arg Arg Glu Gln Arg Leu Cys Ala Asn Arg Lys Leu
    290                 295                 300

Gln Pro Ala Cys Phe Leu Ala Ala Leu Glu Glu Ala Val Val Ala Ser
305                 310                 315                 320

Asp Arg Trp Arg Lys Trp Leu Gln Pro Asp Glu Ile Gly Lys Pro Phe
                325                 330                 335

Ala Glu Leu Thr Pro Ala Arg Arg Trp Leu Val Gln Thr Gly Ala
            340                 345                 350

Arg Tyr Val Trp Thr Ala Pro Lys Val Ile Ala Ala Arg Glu Gln Leu
        355                 360                 365

Tyr Ala His Leu Ser Leu Val Gln Ala Asp Pro His Ala Tyr Val Val
    370                 375                 380
```

```
Glu Ser Val Ala Arg Ser Ile Glu Arg Tyr Ile Asp Ala Phe Asn Leu
385                 390                 395                 400

Tyr Asp Ala Ala Thr Leu Leu Gly
                405
```

<210> SEQ ID NO 18
<211> LENGTH: 1227
<212> TYPE: DNA
<213> ORGANISM: Artificial Sequence
<220> FEATURE:
<223> OTHER INFORMATION: DNA sequence of Tagatose-biphosphate aldolase,
      CJ_CAE_F4E derived from Caldilinea aerophila

<400> SEQUENCE: 18

```
atgtcaacac ttcgccacat cattttgcga ctgatcgagc tgcgtgaacg agaacagatc      60
catctcacgc tgctggccgt ctgtcccaac tcggcggcgg tgctggaggc agcggtgaag     120
gtcgccgcgc gctgccacac gccgatgctc ttcgctgcca cgctcaatca agtcgatcgc     180
gacggcggct acaccggttg gacgcctgcg caattcgtcg ccgagatgcg tcgctatgcc     240
gtccgctatg gctgcaccac cccgctctat ccttgcctgg atcacggcgg ccgtggctc      300
aaagatcgcc atgcacagga aaagctaccg ctcgaccagg cgatgcatga ggtcaagctg     360
agcctcaccg cctgtctgga ggccggctac gcgctgctgc acatcgaccc cacggtcgat     420
cgcacgctcc cgcccggaga agcgccgctc gtgccgatcg tcgtcgagcg cacggtcgag     480
ctgatcgaac atgccgaaca ggagcgacag cggctgaacc tgccggcggt cgcctatgaa     540
gtcggcaccg aagaagtaca tggcgggctg gtgaatttcg acaattttgt cgccttcttg     600
gatttgctca aggcaaggct tgaacaacgt gccctgatgc acgcctggcc cgccttcgtg     660
gtggcgcagg tcggcactga cctgcataca acgtattttg accccagtgc ggcgcaacgg     720
ctgactgaga tcgtgcgccc taccggtgca ctgttgaagg gcactacac cgactgggtc      780
gaaaatcccg ccgactatcc gagggtaggc atgggaggcg ccaacgttgg tccagagttt     840
acggcggccg agttcgaggc gctggaagcg ctggaacggc gggaacaacg gctgtgcgcc     900
aaccggaaat tgcagcccgc ctgttttttg gctgcactgg aagaggcagt agtcgcttca     960
gatcgttggc ggaagtggct ccagcccgat gagatcggca agcccttgc agaattaacg      1020
cccgcacgcc ggcgctggct cgtgcagacc ggggcacgct acgtctggac tgcgccgaaa     1080
gttatcgccg cacgcgaaca gctctatgcg cacctctccc ttgtgcaggc ggatccacat     1140
gcctacgtgg tagagtcagt cgcccggtca atcgagcgct atatcgatgc cttcaactta     1200
tacgacgccg ctacattgct tggatga                                         1227
```

<210> SEQ ID NO 19
<211> LENGTH: 446
<212> TYPE: PRT
<213> ORGANISM: Artificial Sequence
<220> FEATURE:
<223> OTHER INFORMATION: An amino acid sequence of Tagatose-biphosphate
      aldolase, CJ_TATH_F4E derived from Thermoanaerobacter
      thermohydrosulfuricus

<400> SEQUENCE: 19

```
Met Asn Thr Glu His Pro Leu Lys Asn Val Val Lys Leu Gln Lys Lys
1               5                   10                  15

Gly Ile Pro Ile Gly Ile Tyr Ser Val Cys Ser Ala Asn Glu Ile Val
            20                  25                  30
```

```
Ile Gln Val Ala Met Glu Lys Ala Leu Ser Met Asp Ser Tyr Val Leu
            35                  40                  45
Ile Glu Ala Thr Ala Asn Gln Val Asn Gln Tyr Gly Gly Tyr Thr Asn
        50                  55                  60
Met Lys Pro Ile Asp Phe Arg Asp Phe Val Tyr Ser Ile Ala Lys Arg
 65                  70                  75                  80
Ile Asn Phe Pro Glu Asn Arg Ile Ile Leu Gly Gly Asp His Leu Gly
                    85                  90                  95
Pro Leu Pro Trp Lys Asn Gln Gln Ala Lys Lys Ala Met Glu Glu Ala
                100                 105                 110
Lys Glu Leu Val Lys Gln Phe Val Met Ala Gly Phe Thr Lys Ile His
            115                 120                 125
Val Asp Thr Ser Met Leu Leu Gly Asp Asp Asn Ile Asn Ile Lys Leu
        130                 135                 140
Asp Thr Glu Thr Ile Ala Glu Arg Gly Ala Ile Leu Val Ser Val Ala
145                 150                 155                 160
Glu Arg Ala Phe Glu Glu Leu Lys Lys Phe Asn Pro Tyr Ala Leu His
                    165                 170                 175
Pro Val Tyr Val Ile Gly Ser Glu Val Pro Val Pro Gly Gly Ser Gln
                180                 185                 190
Lys Glu Asn Asn Asn Glu Ile Gln Val Thr Lys Pro Thr Asp Phe Glu
            195                 200                 205
Glu Thr Val Glu Val Tyr Lys Ser Thr Phe Tyr Lys Tyr Gly Leu Gly
        210                 215                 220
Asn Ala Trp Glu Asp Val Ala Val Val Gln Ala Gly Val Glu
225                 230                 235                 240
Phe Gly Val Glu Asp Ile His Glu Tyr Asp His Gln Gln Ala Glu Asn
                    245                 250                 255
Leu Val Ser Ala Leu Lys Lys Tyr Pro Asn Leu Val Phe Glu Ala His
                260                 265                 270
Ser Thr Asp Tyr Gln Pro Ala Lys Leu Leu Lys Glu Met Val Arg Asp
            275                 280                 285
Gly Phe Ala Ile Leu Lys Val Gly Pro Glu Leu Thr Phe Ala Leu Arg
        290                 295                 300
Glu Gly Leu Phe Ala Leu Asn Ile Ile Glu Lys Glu Leu Phe Lys Asp
305                 310                 315                 320
Asn His Asp Ile Glu Met Ser Asn Phe Ile Asp Ile Leu Asp Thr Ala
                    325                 330                 335
Met Leu Asn Asn Pro Lys Tyr Trp Glu Gln Tyr Tyr Gly Asp Asp
                340                 345                 350
Asn Lys Ile Arg Ile Ala Arg Lys Tyr Ser Tyr Ser Asp Arg Cys Arg
            355                 360                 365
Tyr Tyr Leu Ile Glu Asn Glu Val Arg Ala Ser Met Ser Arg Leu Phe
        370                 375                 380
Lys Asn Leu Thr Asn Val Glu Ile Pro Leu Thr Leu Ile Ser Gln Tyr
385                 390                 395                 400
Met Pro Ile Gln Tyr Glu Lys Ile Arg Met Gly Leu Leu Lys Asn Asp
                    405                 410                 415
Pro Glu Asn Leu Val Lys Asp Lys Ile Gly Asn Cys Ile Asp Lys Tyr
                420                 425                 430
Leu Tyr Ala Thr Asn Pro Thr Ser Gly Glu Phe Lys Leu Ile
            435                 440                 445
```

<210> SEQ ID NO 20
<211> LENGTH: 1341
<212> TYPE: DNA
<213> ORGANISM: Artificial Sequence
<220> FEATURE:
<223> OTHER INFORMATION: DNA sequence of Tagatose-biphosphate aldolase,
    CJ_TATH_F4E derived from Thermoanaerobacter thermohydrosulfuricus

<400> SEQUENCE: 20

```
atgaatacag aacatccttt gaaaaacgtt gttaaactac aaaaaaaggg aattccaata      60
ggtatttatt cagtttgtag tgcaaatgaa atagttattc aagttgcaat ggagaaggca     120
ttgagtatgg atagttatgt tttaattgaa gcaacggcta atcaagtaaa tcaatatggt     180
ggctatacga atatgaaacc tattgatttt agagattttg tgtattctat agccaaaagg     240
ataaacttcc cagaaaatag aataatcctt ggcggggacc acttaggacc tttgccatgg     300
aaaaatcaac aagcgaaaaa agcaatggaa gaagcaaaag aacttgttaa acaatttgtg     360
atggctggct ttacgaaaat tcatgtagat acaagtatgc ttcttggaga tgataacata     420
aatatcaaac tagatactga aactattgcg gagagaggag cgatacttgt atcagtagca     480
gaaagagctt ttgaggagtt aaaaaagttt aatccttatg ctcttcatcc agtttatgta     540
ataggtagtg aagttcctgt tccaggaggt tctcaaaaag aaaataataa tgaaatacaa     600
gtaacaaagc cgacggattt tgaagaaact gtggaagtgt ataaaagcac tttctataaa     660
tatggtttag gaaacgcatg ggaagatgtt gtagcagtgg ttgtgcaggc tggggtggaa     720
tttggagttg aagatattca tgaatatgat caccaacagg ctgaaaattt agtaagtgct     780
ttaaaaaagt atcctaattt agtatttgaa gcccactcta cggattatca acctgcaaaa     840
ctactaaaag aaatggtgag agatggattt gctatactta agttggacc tgaattgact     900
tttgcattaa gggaaggatt gtttgctctg aatattatag aaaagaatt atttaaagat     960
aatcatgata ttgagatgtc aaattttatt gatatccttg atacagcaat gttaaataat    1020
ccgaagtatt gggaacagta ttattacggt gatgataata aaattagaat tgctagaaaa    1080
tacagctatt ctgatagatg taggtattat ctaatcgaaa atgaagttag agcatctatg    1140
tctaggttgt ttaaaaattt aacaaatgtt gagataccat taaccttgat aagtcagtat    1200
atgcctattc aatatgaaaa aattagaatg ggactattaa aaaatgatcc tgagaattta    1260
gtaaagata aaattggaaa ttgcattgat aagtatttgt atgctactaa tccgacaagt    1320
ggagaattta aactaatata a                                               1341
```

<210> SEQ ID NO 21
<211> LENGTH: 38
<212> TYPE: DNA
<213> ORGANISM: Artificial Sequence
<220> FEATURE:
<223> OTHER INFORMATION: Synthetic primer

<400> SEQUENCE: 21

```
atatacatat gtcaacactt cgccacatca ttttgcga                              38
```

<210> SEQ ID NO 22
<211> LENGTH: 35
<212> TYPE: DNA
<213> ORGANISM: Artificial Sequence
<220> FEATURE:
<223> OTHER INFORMATION: Synthetic primer

```
<400> SEQUENCE: 22
tggtgctcga gtccaagcaa tgtagcggcg tcgta                              35
```

COMPOSITION FOR PRODUCING TAGATOSE AND METHOD OF PRODUCING TAGATOSE USING THE SAME

BACKGROUND OF THE INVENTION

1. Field of the Invention

The present disclosure relates to a composition for producing tagatose, comprising fructose-4-epimerase, and a method of producing tagatose using the same.

2. Description of the Related Art

Tagatose is a natural sweetener, which is present in a small amount in foods such as milk, cheese, cacao, etc., and in sweet fruits such as apples and mandarin. Tagatose has a calorie value of 1.5 kcal/g which is one third that of sucrose, and a glycemic index (GI) of 3 which is 5% that of sucrose. Tagatose has a physical property and a sweet taste similar to sucrose and various health benefits. In this regard, tagatose can be used in a wide variety of products as an alternative sweetener capable of satisfying both taste and health.

Conventionally known or commonly used methods of producing tagatose include a chemical method (a catalytic reaction) or a biological method (an isomerizing enzyme reaction) of using galactose as a main raw material (see PCT WO 2006/058092, Korean Patent Nos. 10-0964091 and 10-1368731). However, the price of lactose which is a basic raw material of galactose used as a main raw material in the known production methods was unstable, depending on produced amounts, supply, and demand of raw milk and lactose in global markets, etc. Thus, there is a limitation in the stable supply thereof. Therefore, a new method capable of producing tagatose from a commonly used sugar (sucrose, glucose, fructose, etc.) as a raw material has been needed and studied, and the above-mentioned documents disclose a method of producing galactose, psicose, and tagatose from glucose, galactose, and fructose, respectively (Korean Patent Nos. 10-744479, 10-1057873, and 10-1550796).

Meanwhile, tagatose-biphosphate aldolase (EC 4.1.2.40) is known to produce glycerone phosphate and D-glyceraldehyde 3-phosphate from D-tagatose 1,6-biphosphate as a substrate, as in the following [Reaction Scheme 1], and to participate in a galactose metabolism. However, there have been no studies regarding whether the tagatose-biphosphate aldolase has activity to produce tagatose.

[Reaction Scheme 1]
D-tagatose 1,6-biphosphate<=>glycerone phosphate+D-glyceraldehyde 3-phosphate Under this background, the present inventors have conducted extensive studies to develop an enzyme having activity to convert fructose into tagatose, and as a result, they found that tagatose-biphosphate aldolase (EC 4.1.2.40) has the ability to convert fructose into tagatose, thereby completing the present disclosure.

SUMMARY OF THE INVENTION

An object of the present disclosure is to provide a composition useful for the production of tagatose, comprising tagatose-biphosphate aldolase, a microorganism expressing the tagatose-biphosphate aldolase, or a culture of the microorganism.

Another object of the present disclosure is to provide a method of producing tagatose, comprising converting fructose into tagatose by contacting fructose with fructose-4-epimerase of the present disclosure, a microorganism expressing the fructose-4-epimerase, or a culture of the microorganism.

Other objects and advantages of the present disclosure will be described in more detail with reference to the following description along with the accompanying claims and drawings. Since contents that are not described in the present specification may be sufficiently recognized and inferred by those skilled in the art or similar art, a description thereof will be omitted.

DETAILED DESCRIPTION OF THE PREFERRED EMBODIMENTS

Figure 1:
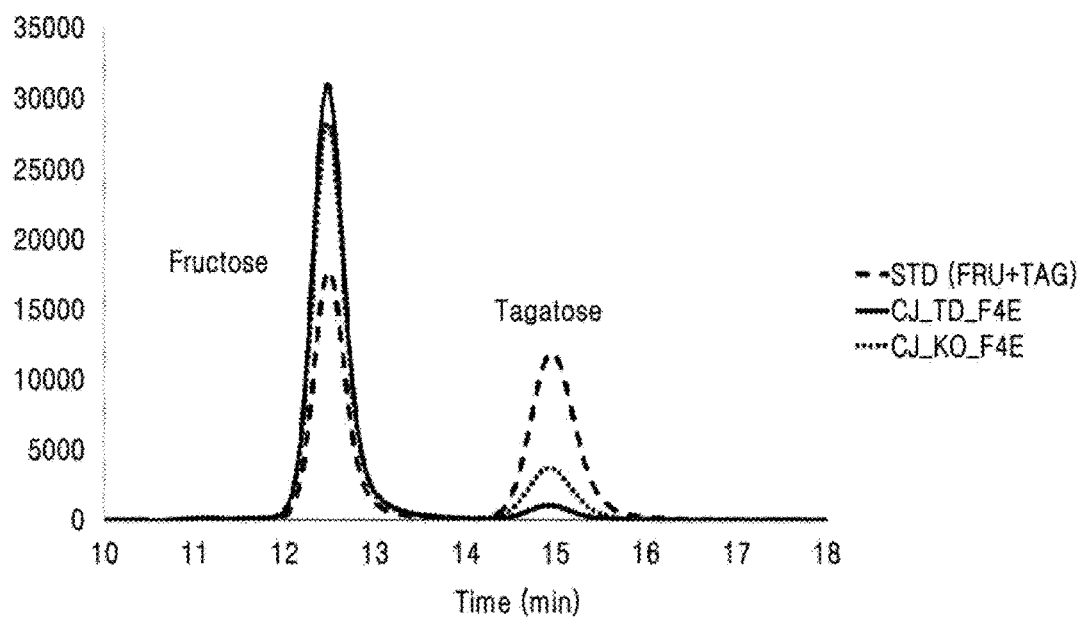
FIG. 1 is a result of HPLC chromatography showing that tagatose-biphosphate aldolases (CJ_TD_F4E and CJ_KO_F4E) prepared in one embodiment of the present disclosure have fructose-4-epimerase activity.

Hereinafter, the present disclosure will be described in detail as follows. Meanwhile, each description and embodiment disclosed in this disclosure may be applied to other descriptions and embodiments. Further, all combinations of various elements disclosed in this disclosure fall within the scope of the present disclosure. Further, the scope of the present disclosure is not limited by the specific description described below.

To achieve objects of the present disclosure, an aspect of the present disclosure provides a composition for producing tagatose, comprising tagatose-biphosphate aldolase, a microorganism expressing the tagatose-biphosphate aldolase, or a culture of the microorganism.

The tagatose-biphosphate aldolase is a tagatose-biphosphate aldolase (EC 4.1.2.40). For example, the tagatose-biphosphate aldolase may be any one without limitation as long as it is able to produce tagatose from fructose as a substrate. Specifically, the tagatose-biphosphate aldolase may have a conversion rate (conversion rate=weight of tagatose/initial weight of fructose*100) of 0.01% or more, specifically, 0.1% or more, and more specifically, 0.3% or more from fructose as a substrate into tagatose. More specifically, the conversion rate may be in the range from 0.01% to 40%, from 0.1% to 30%, from 0.3% to 25%, or from 0.3% to 20%.

Specifically, the tagatose-biphosphate aldolase may comprise a polypeptide consisting of an amino acid sequence of SEQ ID NO: 1, 3, 5, 7, 9, 11, 13, 15, 17, or 19, or a polypeptide having at least 80%, 90%, 95%, 97%, or 99% homology with the amino acid sequence of SEQ ID NO: 1, 3, 5, 7, 9, 11, 13, 15, 17, or 19. It is apparent that a polypeptide having the homology and an amino acid sequence exhibiting the efficacy (i.e., fructose-4-epimerization activity to convert fructose into tagatose by epimerization at C4 position of fructose) corresponding to the protein consisting of the amino acid sequence of SEQ ID NO: 1, 3, 5, 7, 9, 11, 13, 15, 17, or 19 is also included in the scope of the present disclosure, although it has an amino acid sequence, of which a partial sequence is deleted, modified, substituted, or added. Further, a probe which may be produced from the known nucleotide sequence, for example, a polypeptide encoded by a polynucleotide which is hybridizable with a complementary sequence to all or a part of a nucleotide sequence encoding the polypeptide under stringent conditions may be also included without limitation, as long as it has the fructose-4-epimerization activity. Further, the composition may comprise one or more of tagatose-biphosphate aldolase consisting of an amino acid sequences of SEQ ID NO: 1, 3, 5, 7, 9, 11, 13, 15, 17, or 19.

The present disclosure revealed that the 'tagatose-biphosphate aldolase' exhibits the fructose-4-epimerization activity to convert fructose into tagatose by epimerizing fructose at C4 position. In the present disclosure, therefore, the 'tagatose-biphosphate aldolase' may be used interchangeably with 'fructose-4-epimerase'.

As used herein, the term "stringent conditions" mean conditions under which specific hybridization between polynucleotides is allowed. These conditions depend on the length of the polynucleotide and the degree of complementation, and variables are well known in the art, and specifically described in a literature (e.g., J. Sambrook et al., infra). The stringent conditions may include, for example, conditions under which genes having high homology, 80% or higher homology, 90% or higher homology, 95% or higher homology, 97% or higher homology, 99% or higher homology are hybridized with each other and genes having homology lower than the above homology are not hybridized with each other, or ordinary washing conditions of Southern hybridization, i.e., washing once, specifically, twice or three times at a salt concentration and a temperature corresponding to 60° C., 1×SSC, 0.1% SDS, specifically, 60° C., 0.1×SSC, 0.1% SDS, and more specifically 68° C., 0.1×SSC, 0.1% SDS. The probe used in the hybridization may be a part of a complementary sequence of the nucleotide sequence. Such a probe may be produced by PCR using oligonucleotides produced based on the known sequence as primers and a DNA fragment containing these nucleotide sequences as a template. Further, those skilled in the art may adjust the temperature and the salt concentration of the washing solution according to factors such as the length of the probe, if necessary.

As used herein, the term "homology" refers to a percentage of identity between two polynucleotide or polypeptide moieties. Sequence homology from one moiety to another may be determined by a known technique in the art. For example, the homology may be determined by directly aligning the sequence information of two polynucleotide molecules or two polypeptide molecules, e.g., parameters such as score, identity, similarity, etc., using a computer program that is readily available and capable of aligning sequence information (e.g., BLAST 2.0). Additionally, the homology between polynucleotides may be determined by hybridizing the polynucleotides under a condition for forming a stable double-strand in the homologous regions followed by digesting the hybridized strand by a single-strand-specific nuclease to determine the size of digested fragments.

In a specific embodiment, the fructose-4-epimerase of the present disclosure may be an enzyme derived from a heat-resistant microorganism, for example, an enzyme derived from *Thermanaerothrix* sp. or a variant thereof, an enzyme derived from *Kosmotoga* sp. or a variant thereof, an enzyme derived from *Rhodothermus* sp. or a variant thereof, an enzyme derived from *Limnochorda* sp. or a variant thereof, an enzyme derived from *Caldithrix* sp., *Caldilinea* sp., *Thermoanaerobacter* sp., *Acidobacteriales* sp., or *Caldicellulosiruptor* sp. or a variant thereof. Specifically, the fructose-4-epimerase of the present disclosure may be an enzyme derived from *Thermanaerothrix daxensis, Kosmotoga olearia, Rhodothermus profundi, Rhodothermus marinus, Limnochorda pilosa, Caldithrix abyssi, Caldilinea aerophila, Thermoanaerobacter thermohydrosulfuricus, Acidobacteriales bacterium,* or *Caldicellulosiruptor kronotskyensis,* or a variant thereof. More specifically, the fructose-4-epimerase of the present disclosure may be an enzyme derived from *Rhodothermus profundi* DSM 22212 or *Rhodothermus marinus* ATCC 43812, or a variant thereof.

The fructose-4-epimerase of the present disclosure or a variant thereof is characterized by converting D-fructose into D-tagatose by epimerizing D-fructose at C4 position. It is known that the fructose-4-epimerase has tagatose-biphosphate aldolase activity, produces glycerone phosphate and D-glyceraldehyde 3-phosphate from D-tagatose 1,6-biphosphate as a substrate, and participates in a galactose metabolism. The present disclosure newly revealed that the tagatose-biphosphate aldolase has the fructose-4-epimerase activity. Accordingly, one embodiment of the present disclosure relates to novel use of the tagatose-biphosphate aldolase including using the tagatose-biphosphate aldolase as the fructose-4-epimerase in the production of tagatose from fructose. Further, another embodiment of the present disclosure relates to a method of producing tagatose from fructose using the tagatose-biphosphate aldolase as the fructose-4-epimerase.

In one embodiment, the fructose-4-epimerase of the present disclosure may be an enzyme having high heat resistance. Specifically, the fructose-4-epimerase of the present disclosure may exhibit 50% to 100%, 60% to 100%, 70% to 100%, or 75% to 100% of its maximum activity at 50° C. to 70° C. More specifically, the fructose-4-epimerase of the present disclosure may exhibit 80% to 100% or 85% to 100% of its maximum activity at 55° C. to 60° C., 60° C. to 70° C., 55° C., 60° C., or 70° C.

Furthermore, the fructose-4-epimerase consisting of SEQ ID NO: 1 may be encoded by a nucleotide sequence of SEQ ID NO: 2; the fructose-4-epimerase consisting of SEQ ID NO: 3 may be encoded by a nucleotide sequence of SEQ ID NO: 4; the fructose-4-epimerase consisting of SEQ ID NO: 5 may be encoded by a nucleotide sequence of SEQ ID NO: 6; the fructose-4-epimerase consisting of SEQ ID NO: 7 may be encoded by a nucleotide sequence of SEQ ID NO: 8; the fructose-4-epimerase consisting of SEQ ID NO: 9 may be encoded by a nucleotide sequence of SEQ ID NO: 10; the fructose-4-epimerase consisting of SEQ ID NO: 11 may be encoded by a nucleotide sequence of SEQ ID NO: 12; the fructose-4-epimerase consisting of SEQ ID NO: 13 may be encoded by a nucleotide sequence of SEQ ID NO: 14; the fructose-4-epimerase consisting of SEQ ID NO: 15 may be encoded by a nucleotide sequence of SEQ ID NO: 16; the fructose-4-epimerase consisting of SEQ ID NO: 17 may be encoded by a nucleotide sequence of SEQ ID NO: 18; and the fructose-4-epimerase consisting of SEQ ID NO: 19 may be encoded by a nucleotide sequence of SEQ ID NO: 20, but are not limited thereto.

The fructose-4-epimerase of the present disclosure or a variant thereof may be obtained by transforming a microorganism such as *E.coli* with DNA expressing the enzyme of the present disclosure or the variant thereof, e.g., SEQ ID NO: 2, 4, 6, 8, 10, 12, 14, 16, 18, 19 or 20, culturing the microorganism to obtain a culture, disrupting the culture, and then performing purification using a column, etc. The microorganism for transformation may include *Corynebacterium glutamicum, Aspergillus oryzae,* or *Bacillus subtilis,* in addition to *Escherichia coli.*

In a specific embodiment, the transformed microorganism may be *E.coli* BL21(DE3)/CJ_TD_F4E, *E.coli* BL21(DE3)/CJ_KO_F4E, *E.coli* BL21(DE3)/CJ_RP_F4E, *E.coli* BL21(DE3)/CJ_RM_F4E, *E.coli* BL21(DE3)/CJ_LP_F4E, *E.coli* BL21(DE3)/CJ_Cab_F4E, *E.coli* BL21(DE3)/CJ_Ckr, *E.coli* BL21(DE3)/CJ_CAE_F4E, *E.coli* BL21(DE3)/CJ_TATH_F4E, or *E.coli* BL21(DE3)/CJ_AB_F4E, and these microorganisms were deposited at the Korean Culture Center of Microorganisms which is an International Depositary Authority under the provisions of the Budapest Treaty with Accession Nos. KCCM11995P (date of deposit: Mar. 20, 2017), KCCM11999P (date of deposit: Mar. 24, 2017), KCCM12097P (date of deposit: Aug. 11, 2017), KCCM12096P (date of deposit: Aug. 11, 2017), KCCM12095P (date of deposit: Aug. 11, 2017), KCCM12107P (date of deposit: Sep. 13, 2017), KCCM12108P (date of deposit: Sep. 13, 2017), KCCM12233P (date of deposit: Mar. 23, 2018), KCCM12234P (date of deposit: Mar. 23, 2018), and KCCM12237P (date of deposit: Mar. 23, 2018), respectively.

The fructose-4-epimerase used in the present disclosure may be provided by using a nucleic acid encoding the same.

As used herein, the term "nucleic acid" means that it encompasses DNA or RNA molecules, wherein nucleotides which are basic constituent units in the nucleic acid may include not only natural nucleotides but also analogues with modification of sugar or base (see: Scheit, Nucleotide Analogs, John Wiley, New York(1980); Uhlman and Peyman, Chemical Reviews, 90:543-584(1990)).

The nucleic acid of the present disclosure may be a nucleic acid encoding the polypeptide consisting of the amino acid sequence of SEQ ID NO: 1, 3, 5, 7, 9, 11, 13, 15, 17, or 19 of the present disclosure or a nucleic acid encoding a polypeptide having at least 80%, 90%, 95%, 97% or 99% homology with the fructose-4-epimerase of the present disclosure and having the fructose-4-epimerase activity. For example, the nucleic acid encoding the fructose-4-epimerase consisting of the amino acid sequence of SEQ ID NO: 1 may be a nucleic acid having at least 80%, 90%, 95%, 97%, 99% or 100% homology with the nucleotide sequence of SEQ ID NO: 2. Further, for example, the nucleic acid encoding the fructose-4-epimerase consisting of the amino acid sequence of SEQ ID NO: 3 may be a nucleic acid having at least 80%, 90%, 95%, 97%, 99% or 100% homology with the nucleotide sequence of SEQ ID NO: 4. This may be also applied to nucleic acids encoding the enzymes having other amino acid sequences described herein. It is also apparent that the nucleic acid of the present disclosure may include a nucleic acid which is translated into the fructose-6-phosphate-4-epimerase of the present disclosure due to codon degeneracy or a nucleic acid which hybridizes with a nucleic acid consisting of a nucleotide sequence complementary to the nucleotide sequence of SEQ ID NO: 2, 4, 6, 8, 10, 12, 14, 16, 18, or 20 under stringent conditions and encodes the polypeptide having the fructose-6-phosphate-4-epimerase activity of the present disclosure. The microorganism expressing the fructose-4-epimerase which may be used in the present disclosure may be a microorganism including a recombinant vector including the nucleic acid. The vector may be operably linked to the nucleic acid of the present disclosure. As used herein, the term "operably linked" means that a nucleotide expression regulatory sequence and a nucleotide sequence encoding a desired protein are operably linked to each other to perform the general functions, thereby affecting expression of the encoding nucleotide sequence. The operable linkage to the vector may be produced using a genetic recombination technology known in the art, and the site-specific DNA cleavage and linkage may be produced using restriction enzymes and ligases known in the art. As used herein, the term "vector" refers to any mediator for cloning and/or transferring of bases into an organism, such as a host cell. The vector may be a replicon that is able to bring the replication of combined fragments in which different DNA fragments are combined. Here, the term "replicon" refers to any genetic unit (e.g., plasmid, phage, cosmid, chromosome, virus) which functions as a self-unit of DNA replication in vivo, i.e., which is able to be replicated by self-regulation. As used herein, the term "vector" may include viral and non-viral mediators for introducing the bases into the organism, e.g., a host cell, in vitro, ex vivo, or in vivo, and may also include a minicircular DNA, a transposon such as Sleeping Beauty (Izsvak et al. J. Mol. Biol. 302:93-102 (2000)), or an artificial chromosome. Examples of the vector commonly used may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc., may be used; and as a plasmid vector, those based on pBR, pUC, pBluescriptII, pGEM, pTZ, pCL, pET, etc., may be used. The vectors that may be used in the present disclosure are not particularly limited, but any known expression vector may be used. Further, the vector may be a recombinant vector characterized by further including various antibiotic resistance genes. As used herein, the term "antibiotic resistance gene" refers to a gene having resistance against an antibiotic, and a cell having this gene survives in an environment treated with the corresponding antibiotic. Thus, the antibiotic resistance gene is used as a selectable marker during production of a large amount of plasmids in *E.coli*. The antibiotic resistance gene in the present disclosure is not a factor that greatly influences expression efficiency according to optimal combinations of vectors which is a key technology of the present disclosure, and thus an antibiotic resistance gene that is generally used as a selectable marker may be used without limitation. Specific examples may include a resistance gene against ampicilin, tetracyclin, kanamycin, chloroamphenicol, streptomycin, or neomycin.

The microorganism expressing the fructose-4-epimerase which may be used in the present disclosure may be obtained by a method of introducing the vector including the nucleic acid encoding the enzyme into a host cell, and a method of transforming the vector may be any method as long as it is able to introduce the nucleic acid into the cell. An appropriate standard technique known in the art may be selected and performed. Electroporation, calcium phosphate co-precipitation, retroviral infection, microinjection, a DEAE-dextran method, a cationic liposome method, and a heat shock method may be included, but is not limited thereto.

As long as the transformed gene may be expressed in the host cell, it may be integrated into and placed in the chromosome of the host cell, or it may exist extrachromosomally. Further, the gene includes DNA and RNA as a polynucleotide encoding a polypeptide, and any form may be used without limitation, as long as it may be introduced into the host cell and expressed therein. For example, the gene may be introduced into the host cell in the form of an expression cassette, which is a polynucleotide construct including all elements required for its autonomous expression. Commonly, the expression cassette includes a promoter operably linked to the gene, transcriptional termination signals, ribosome binding sites, and translation termination signals. The expression cassette may be in the form of a self-replicable recombinant vector. Also, the gene as it is or in the form of a polynucleotide construct may be introduced into the host cell and operably linked to sequences required for expression in the host cell.

The microorganism of the present disclosure may include either a prokaryotic microorganism or a eukaryotic microorganism, as long as it is a microorganism capable of producing the fructose-4-epimerase of the present disclosure by including the nucleic acid of the present disclosure or the recombinant vector of the present disclosure. For example, the microorganism may include microorganism strains belonging to the genus *Escherichia*, the genus *Erwinia*, the genus *Serratia*, the genus *Providencia*, the genus *Corynebacterium*, and the genus *Brevibacterium*, and specifically, it may be *E.coli* or *Corynebacterium glutamicum*, but is not limited thereto. Specific examples of the microorganism may include *E.coli* BL21(DE3)/CJ_TD_F4E, *E.coli* BL21(DE3)/CJ_KO_F4E, *E.coli* BL21(DE3)/CJ_RP_F4E, *E.coli* BL21(DE3)/CJ_RM_F4E, *E.coli* BL21(DE3)/CJ_LP_F4E, *E.coli* BL21(DE3)/CJ_Cab_F4E, *E.coli* BL21(DE3)/CJ_Ckr_F4E, *E.coli* BL21(DE3)/CJ_CAE_F4E, *E.coli* BL21(DE3)/CJ_TATH_F4E, and *E.coli* BL21(DE3)/CJ_AB_F4E.

The microorganism of the present disclosure may include any microorganism capable of expressing the fructose-4-epimerase of the present disclosure according to various known methods, in addition to introduction of the nucleic acid or the vector.

The culture of the microorganism of the present disclosure may be produced by culturing, in a medium, the microorganism capable of expressing the tagatose-biphosphate aldolase of the present disclosure.

As used herein, the term "culturing" means that the microorganism is allowed to grow under appropriately controlled environmental conditions. The culturing process of the present disclosure may be carried out according to an appropriate medium and culture conditions known in the art. The culturing process may be easily adjusted by those skilled in the art according to the strain to be selected. The step of culturing the microorganism may be, but is not particularly limited to, carried out by a known batch process, a continuous process, or a fed batch process. With regard to the culture conditions, a proper pH (e.g., pH 5 to 9, specifically pH 7 to 9) may be adjusted using a basic compound (e.g., sodium hydroxide, potassium hydroxide, or ammonia) or an acidic compound (e.g., phosphoric acid or sulfuric acid), but is not particularly limited thereto. Additionally, an antifoaming agent such as fatty acid polyglycol ester may be added during the culturing process to prevent foam generation. Additionally, oxygen or an oxygen-containing gas may be injected into the culture in order to maintain an aerobic state of the culture; or nitrogen, hydrogen, or carbon dioxide gas may be injected without the injection of a gas in order to maintain an anaerobic or microaerobic state of the culture. The culture temperature may be maintained from 25° C. to 40° C., and specifically, from 30° C. to 37° C., but is not limited thereto. The culturing may be continued until the desired amount of useful materials is obtained, and specifically for about 0.5 hours to about 60 hours, but is not limited thereto. Furthermore, the culture medium to be used may include, as sugar sources, sugars and carbohydrates (e.g., glucose, sucrose, lactose, fructose, maltose, molasses, starch, and cellulose), oils and fats (e.g., soybean oil, sunflower oil, peanut oil, and coconut oil), fatty acids (e.g., palmitic acid, stearic acid, and linoleic acid), alcohols (e.g., glycerol and ethanol), and organic acids (e.g., acetic acid). These substances may be used individually or in a mixture, but are not limited thereto. Nitrogen sources may include nitrogen-containing organic compounds (e.g., peptone, yeast extract, meat extract, malt extract, corn steep liquor, soybean meal, and urea) or inorganic compounds (e.g., ammonium sulfate, ammonium chloride, ammonium phosphate, ammonium carbonate, and ammonium nitrate). These nitrogen sources may also be used individually or in a mixture, but are not limited thereto. Phosphorus sources may include potassium dihydrogen phosphate, dipotassium hydrogen phosphate, or the corresponding sodium salts. These phosphorus sources may also be used individually or in a mixture, but are not limited thereto. The culture medium may include essential growth stimulators, such as metal salts (e.g., magnesium sulfate or iron sulfate), amino acids, and vitamins.

The composition for producing tagatose of the present disclosure may further include fructose.

The composition for producing tagatose of the present disclosure may include tagatose-biphosphate aldolase having fructose-4-epimerization activity to directly convert fructose into tagatose, a microorganism expressing the tagatose-biphosphate aldolase, or a culture of the microorganism, the composition characterized by not including other enzymes than fructose as a substrate.

For example, the composition for producing tagatose of the present disclosure may be characterized by not including, for example, α-glucan phosphorylase, starch phosphorylase, maltodextrin phosphorylase, or sucrose phosphorylase, a microorganism expressing the α-glucan phosphorylase, starch phosphorylase, maltodextrin phosphorylase, or sucrose phosphorylase, or a culture of the microorganism;

glucokinase, a microorganism expressing the glucokinase, or a culture of the microorganism;

tagatose-6-phosphate phosphatase, a microorganism expressing the tagatose-6-phosphate phosphatase, or a culture of the microorganism; and/or α-amylase, pullulanase, glucoamylase, sucrase, or isoamylase; a microorganism expressing the α-amylase, pullulanase, glucoamylase, sucrase, or isoamylase; or a culture of the microorganism expressing the α-amylase, pullulanase, glucoamylase, sucrase, or isoamylase.

The composition for producing tagatose of the present disclosure may further include any suitable excipient commonly used in the corresponding composition for producing tagatose. The excipient may include, for example, a preservative, a wetting agent, a dispersing agent, a suspending agent, a buffer, a stabilizing agent, an isotonic agent, etc., but is not limited thereto.

The composition for producing tagatose of the present disclosure may further include a metal. In one embodiment, the metal of the present disclosure may be a metal containing a divalent cation. Specifically, the metal of the present disclosure may be nickel, magnesium (Mg), or manganese (Mn). More specifically, the metal of the present disclosure may be a metal ion or a metal salt, and much more specifically, the metal salt may be $MgSO_4$, $NiSO_4$, $NiCl_2$, $MgCl_2$, $MnCl_2$, or $MnSO_4$.

Still another aspect of the present disclosure provides a method of producing tagatose, comprising converting D-fructose into tagatose by contacting D-fructose with fructose-4-epimerase of the present disclosure, the microorganism expressing the fructose-4-epimerase, or the culture of the microorganism.

In one embodiment, the contacting of the present disclosure may be performed under conditions of pH 5.0 to pH 9.0 and 30° C. to 80° C. and/or for 0.5 hours to 48 hours.

Specifically, the contacting of the present disclosure may be performed under a condition of pH 6.0 to pH 9.0 or pH 7.0 to pH 9.0. Further, the contacting of the present disclosure may be performed under a temperature condition of 35° C. to 80° C., 40° C. to 80° C., 45° C. to 80° C., 50° C. to 80° C., 55° C. to 80° C., 60° C. to 80° C., 30° C. to 70° C., 35° C. to 70° C., 40° C. to 70° C., 45° C. to 70° C., 50° C. to 70° C., 55° C. to 70° C., 60° C. to 70° C., 30° C. to 65° C., 35° C. to 65° C., 40° C. to 65° C., 45° C. to 65° C., 50° C. to 65° C., 55° C. to 65° C., 30° C. to 60° C., 35° C. to 60° C., 40° C. to 60° C., 45° C. to 60° C., 50° C. to 60° C. or 55° C. to 60° C. Furthermore, the contacting of the present disclosure may be performed for 0.5 hours to 36 hours, 0.5 hours to 24 hours, 0.5 hours to 12 hours, 0.5 hours to 6 hours, 1 hour to 48 hours, 1 hour to 36 hours, 1 hour to 24 hours, 1 hour to 12 hours, 1 hour to 6 hours, 3 hours to 48 hours, 3 hours to 36 hours, 3 hours to 24 hours, 3 hours to 12 hours, 3 hours to 6 hours, 6 hours to 48 hours, 6 hours to 36 hours, 6 hours to 24 hours, 6 hours to 12 hours, 12 hours to 48 hours, 12 hours to 36 hours, 12 hours to 24 hours, 18 hours to 48 hours, 18 hours to 36 hours, or 18 hours to 30 hours.

In one embodiment, the contacting of the present disclosure may be performed in the presence of a metal. The applicable metal is the same as those in the above-described embodiment.

The production method of the present disclosure may further include separating and/or purifying the produced tagatose. The separation and/or purification may be a method commonly used in the art. Non-limiting examples may include dialysis, precipitation, adsorption, electrophoresis, ion exchange chromatography, fractional crystallization, etc. The purification method may be performed only by a single method or by two or more methods.

In addition, the production method of the present disclosure may further include the step of performing decolorization and/or desalination, before or after the separation and/or purification step(s). By performing the decolorization and/or desalination, it is possible to obtain tagatose with higher quality.

In still another embodiment, the production method of the present disclosure may further include the step of performing crystallization of tagatose, after the step of converting into tagatose of the present disclosure, performing the separation and/or purification, or performing the decolorization and/or desalination. The crystallization may be performed by a crystallization method commonly used. For example, the crystallization may be performed by cooling crystallization.

In still another embodiment, the production method of the present disclosure may further include the step of concentrating tagatose, before the crystallization. The concentrating may increase the crystallization efficiency.

In still another embodiment, the production method of the present disclosure may further include the step of contacting unreacted fructose with the enzyme of the present disclosure, the microorganism expressing the enzyme, or the culture of the microorganism after separation and/or purification, the step of reusing a crystal-separated mother solution in the separation and/or purification after the crystallization of the present disclosure, or a combination thereof. The additional steps are economically advantageous in that tagatose may be obtained with higher yield and the amount of fructose to be discarded may be reduced.

Hereinafter, the present disclosure will be described in more detail with reference to Examples. However, the following Examples of the present disclosure are merely an example of the present disclosure. It will be apparent to those skilled in the art that these Examples are for the purpose of illustrating the present disclosure in more detail and the scope of the present disclosure as set forth in the appended claims is not limited by these Examples.

EXAMPLE 1

Production of Tagatose-Biphosphate Aldolase and Evaluation of its Activity

EXAMPLE 1-1

Production of Recombinant Expression Vectors and Transformants Including Tagatose-Biphosphate Aldolase Gene To provide a novel heat-resistant fructose-4-epimerase, information of tagatose-biphosphate aldolase genes derived from *Thermanaerothrix daxensis* and *Kosmotoga olearia* was obtained to prepare vectors expressible in *E.coli* and transformed microorganisms (transformants).

In detail, a nucleotide sequence of tagatose-biphosphate aldolase was selected from nucleotide sequences of three kinds of microorganisms, *Thermanaerothrix daxensis*, *Anaerolinea thermophila*, and *Kosmotoga olearia*, which are registered in KEGG (Kyoto Encyclopedia of Genes and Genomes), and based on an amino acid sequence (SEQ ID NO: 1) and a nucleotide sequence (SEQ ID NO: 2) of *Thermanaerothrix daxensis*, and an amino acid sequence (SEQ ID NO: 5) and a nucleotide sequence (SEQ ID NO: 6) of *Kosmotoga olearia*, recombinant expression vectors prepared by inserting into pBT7-C-His which is a vector expressible in *E.coli* were synthesized in Bioneer Corp.

To induce protein expression, each vector was transformed into BL21(DE3) which is a strain for expression in *E.coli*, and designated as *E.coli* BL21(DE3)/CJ_TD_F4E and *E.coli* BL21(DE3)/CJ_KO_F4E, respectively. *E.coli* BL21(DE3)/CJ_TD_F4E and *E.coli* BL21(DE3)/CJ_KO_F4E were deposited at the Korean Culture Center of Microorganisms under the provisions of the Budapest Treaty with Accession No. KCCM11995P on Mar. 20, 2017, and Accession No. KCCM11999P on Mar. 24, 2017, respectively.

EXAMPLE 1-2

Production and Purification of Recombinant Enzymes

To produce recombinant enzymes, each of *E.coli* BL21(DE3)/CJ_TD_F4E and *E.coli* BL21(DE3)/CJ_KO_F4E which are the transformants produced in Example 1-1 was seeded in a culture tube containing 5 mL of an LB liquid medium with ampicillin, and then seed culture was performed in a shaking incubator at 37° C. until absorbance at 600 nm reached 2.0. Each of the cultures obtained by the seed culture was seeded in a culture flask containing a liquid medium containing LB and lactose which is a protein expression regulator, and then main culture was performed. During the culture, a shaking speed was maintained at 180 rpm and a culture temperature was maintained at 37° C. Each culture was centrifuged at 8,000 rpm and 4° C. for 20 minutes to recover cells. The recovered cells were washed with 50 mM Tris-HCl (pH 8.0) buffer twice and re-suspended in 50 mM $NaH_2PO_4$ (pH 8.0) buffer containing 10 mM imidazole and 300 mM NaCl. The re-suspended cells were disrupted using a sonicator. Cell lysates were centrifuged at 13,000 rpm and 4° C. for 20 minutes to obtain only supernatants. Each supernatant was purified by His-tag affinity chromatography, and 10 column volumes of 50 mM $NaH_2PO_4$ (pH 8.0) buffer containing 20 mM imidazole and 300 mM NaCl was applied to remove non-specifically bound proteins. Next, 50 mM $NaH_2PO_4$ (pH 8.0) buffer containing 250 mM imidazole and 300 mM NaCl was further applied to perform elution. Dialysis was performed using 50 mM Tris-HCl (pH 8.0) buffer to obtain enzymes for enzyme characterization.

EXAMPLE 1-3

Evaluation of Activity to Convert Fructose into Tagatose

To measure activities of the enzymes obtained in Example 1-2, 30% by weight of fructose was used, and 50 mM Tris-HCl (pH 8.0), 1 mM $CoSO_4$, and 20 mg/mL of purified enzyme separated in Example 2 were added thereto, and allowed to react at 60° C. for 2 hours. Concentrations of tagatose converted by three kinds of fructose-4-epimerases, CJ_TD_F4E, and CJ_KO_F4E, and conversion rates from fructose to tagatose were examined, and as a result, CJ_TD_F4E showed a conversion rate of 4.6%, and CJ_KO_F4E showed a conversion rate of 16.0%. These conversion rates were calculated by the following equation: conversion rate =weight of tagatose /initial weight of fructose×100

Further, fructose remaining after reaction and a product tagatose were quantified by HPLC. Shodex Sugar SP0810 was used as a column, and a temperature of the column was 80° C., and water as a mobile phase was applied at a flow rate of 1 mL/min. In FIG. 1, a peak that represents the reaction of the enzyme using fructose as a substrate was detected and quantified by HPLC chromatography.

EXAMPLE 1-4

Effect of Temperature on Fructose-4-Epimerization Activity

Figure 2:
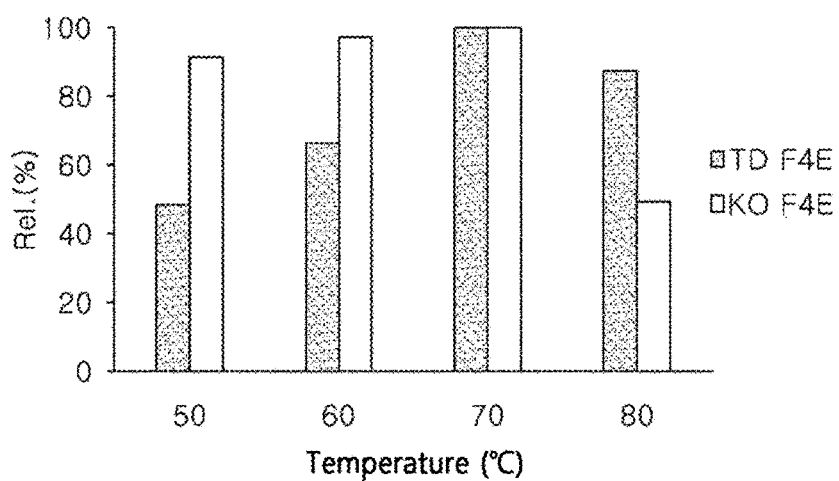
FIG. 2 is a graph showing fructose-4-epimerization activities of tagatose-biphosphate aldolases (CJ_TD_F4E and CJ_KO_F4E) prepared in one embodiment of the present disclosure according to temperature changes.

To examine an effect of temperature on the epimerization activities of the enzymes of the present disclosure, each 1 mg/mL of the purified enzymes produced in Example 1-2 was added to 50 mM Tris HCl (pH 8.0) buffer containing fructose, and allowed to react at 50° C. to 80° C. for 3 hours. Tagatose in each of the reacted solutions was quantified by HPLC. As a result, both of the two enzymes of the present disclosure showed their maximum activities at 70° C. (FIG. 2).

EXAMPLE 2

Production of Tagatose-Biphosphate Aldolase and Evaluation of its Activity

EXAMPLE 2-1

Production of Recombinant Expression Vectors and Transformants Including Tagatose-Biphosphate Aldolase Gene To identify a novel heat-resistant fructose-4-epimerase according to the present disclosure, information of tagatose-biphosphate aldolase genes derived from Rhodothermus profundi DSM 22212 and *Rhodothermus marinus* ATCC 43812 was obtained to prepare vectors expressible in *E.coli* and transformed microorganisms.

In detail, a nucleotide sequence of tagatose- biphosphate aldolase was selected from nucleotide sequences of *Rhodothermus profundi* DSM22212 and *Rhodothermus marinus*

ATCC 43812, which are registered in KEGG (Kyoto Encyclopedia of Genes and Genomes) and NCBI (National Center for Biotechnology Information), and based on amino acid sequences (SEQ ID NOS: 7 and 9) and nucleotide sequences (SEQ ID NOS: 8 and 10) of the two kinds of the microorganisms, pBT7-C-His-CJ_RP_F4E and pBT7-C-His-CJ_RM_F4E which are recombinant vectors containing each of the nucleotide sequence of the enzyme and expressible in E.coli were produced (Bioneer Corp., Korea).

Each of the produced recombinant vectors was transformed into E.coli BL21(DE3) by heat shock transformation (Sambrook and Russell: Molecular cloning, 2001), and frozen and stored in 50% glycerol. The transformants were designated as E.coli BL21(DE3)/CJ_RP_F4E and E.coli BL21(DE3)/CJ_RM_F4E, respectively and deposited at the Korean Culture Center of Microorganisms (KCCM) which is an international depositary authority under the provisions of the Budapest Treaty on Aug. 11, 2017 with Accession Nos. KCCM12097P and KCCM12096P, respectively.

EXAMPLE 2-2

Production and Purification of Recombinant Enzymes

To produce recombinant enzymes from E.coli BL21(DE3)/CJ_RP_F4E and E.coli BL21(DE3)/CJ_RM_F4E which are the transformants produced in Example 2-1, each of the transformants was seeded in a culture tube containing 5 mL of an LB liquid medium with ampicillin antibiotic, and then seed culture was performed in a shaking incubator at 37° C. until absorbance at 600 nm reached 2.0. Each of the cultures obtained by the seed culture was seeded in a culture flask containing a liquid medium containing LB and lactose which is a protein expression regulator, and then main culture was performed. The seed culture and the main culture were performed under conditions of 180 rpm and 37° C. Then, each culture was centrifuged at 8,000 rpm and 4° C. for minutes to recover cells. The recovered cells were washed with 50 mM Tris-HCl (pH 8.0) buffer twice and re-suspended in 50 mM $NaH_2PO_4$ (pH 8.0) buffer containing 10 mM imidazole and 300 mM NaCl. The re-suspended cells were disrupted using a sonicator. Cell lysates were centrifuged at 13,000 rpm and 4° C. for 20 minutes to take only supernatants. Each supernatant was purified by His-tag affinity chromatography, and 10 column volumes of 50 mM $NaH_2PO_4$ (pH 8.0) buffer containing 20 mM imidazole and 300 mM NaCl was applied to remove non-specifically bound proteins. Next, 50 mM $NaH_2PO_4$ (pH 8.0) buffer containing 250 mM imidazole and 300 mM NaCl was further applied to perform elution. Dialysis was performed using 50 mM Tris-HCl (pH 8.0) buffer to obtain CJ_RP_F4E and CJ_RM_F4E which are purified enzymes for enzyme characterization.

EXAMPLE 2-3

Conversion of Fructose into Tagatose and Evaluation of Activity

To measure fructose-4-epimerization activities of CJ_RP_F4E and CJ_RM_F4E which are the recombinant enzymes of the present disclosure obtained in Example 2-2, 50 mM Tris-HCl (pH 8.0), 1 mM $NiSO_4$, and 20 mg/mL of each of CJ_RP_F4E and CJ_RM_F4E were added to 30% by weight of fructose, and allowed to react at 60° C. for 10 hours.

Figure 3:
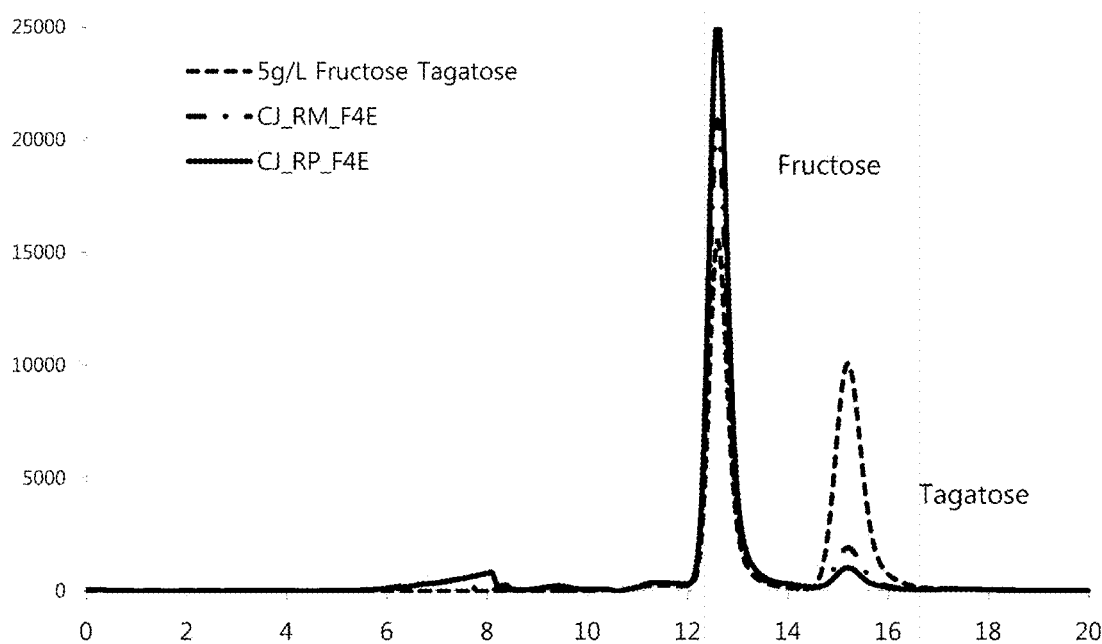
FIG. 3 is a graph of HPLC chromatography showing that tagatose-biphosphate aldolases (CJ_RP_F4E and CJ_RM_F4E) prepared in one embodiment of the present disclosure have fructose-4-epimerase activity.

Further, fructose remaining after reaction and a product tagatose were quantified by HPLC. HPLC was performed by using Shodex Sugar SP0810 as a column, and a temperature of the column was 80° C., and water as a mobile phase was applied at a flow rate of 1 mL/min (FIG. 3).

As a result, it was confirmed that the conversion rates from fructose into tagatose by CJ_RP_F4E and CJ_RM_F4E of the present disclosure were 5.7% and 11.1%, respectively.

EXAMPLE 2-4

Examination of Activities of Recombinant Enzymes According to Temperature

To examine an effect of temperature on the fructose-4-epimerization activities of CJ_RP_F4E and CJ_RM_F4E prepared in Example 2-2, each 1 mg/mL of CJ_RP_F4E and CJ_RM_F4E was added to 50 mM Tris HCl (pH 8.0) buffer containing 10% by weight of fructose, and allowed to react at different temperatures of 45° C., 50° C., 55° C., 60° C., 65° C., and 70° C. for 3 hours. Tagatose in each of the reacted solutions was quantified by HPLC.

Figure 4A:
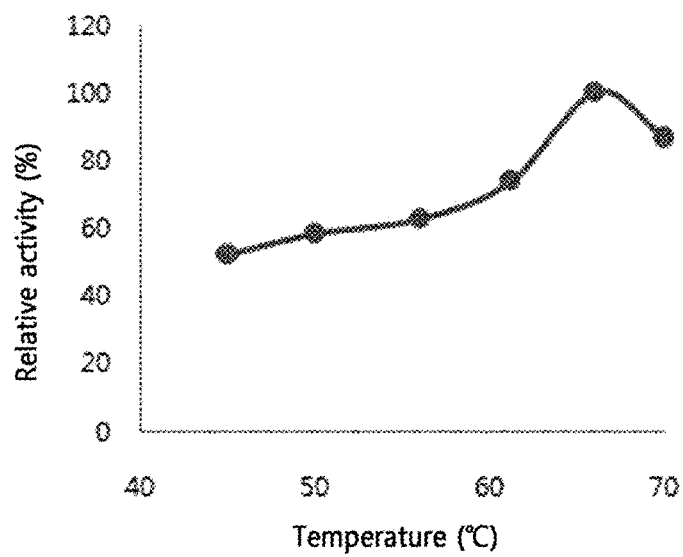
FIG. 4A is a graph showing fructose-4-epimerization activity of tagatose-biphosphate aldolase (CJ_RP_F4E) prepared in one embodiment of the present disclosure according to temperature changes.
Figure 4B:
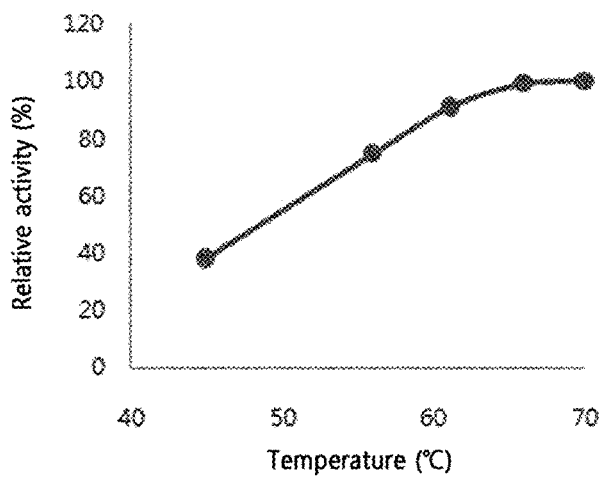
FIG. 4B is a graph showing fructose-4-epimerization activity of tagatose-biphosphate aldolase (CJ_RM_F4E) prepared in one embodiment of the present disclosure according to temperature changes.

As a result, CJ_RP_F4E showed its maximum activity at 65° C., and maintained 70% or more of its maximum activity at 60° C. to 70° C. and 50% or more of its maximum activity in all temperature ranges (FIG. 4A). CJ_RM_F4E showed its maximum activity at 70° C., and maintained 70% or more of its maximum activity at 55° C. to 70° C. and 40% or more of its maximum activity in all temperature ranges (FIG. 4B).

EXAMPLE 2-5

Examination of Activities of Recombinant Enzymes of the Present Disclosure According to Addition of Metal Ion To examine effects of metal ions on the fructose-4-epimerization activities of CJ_RP_F4E and CJ_RM_F4E prepared in Example 2-2, each 1 mg/mL of CJ_RP_F4E and CJ_RM_F4E and each 1 mM of various metal ions ($ZnSO_4$, $MgCl_2$, $MnCl_2$, $NH_4Cl$, $CaCl_2$, $Na_2SO_4$, $CuSO_4$, $MgSO_4$, $MnSO_4$, $(NH_4)_2SO_4$, or $NiSO_4$) were added to 50 mM Tris HCl (pH 8.0) buffer containing 10% by weight of fructose, and allowed to react at 60° C. for 5 hours. Tagatose in each of the reacted solutions was quantified by HPLC.

Figure 5A:
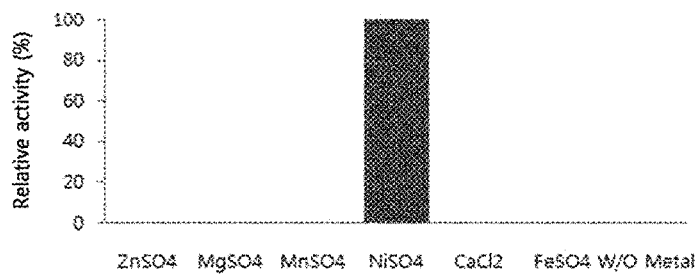
FIG. 5A is a graph showing fructose-4-epimerization activity of tagatose-biphosphate aldolase (CJ_RP_F4E) prepared in one embodiment of the present disclosure according to addition of metals.
Figure 5B:
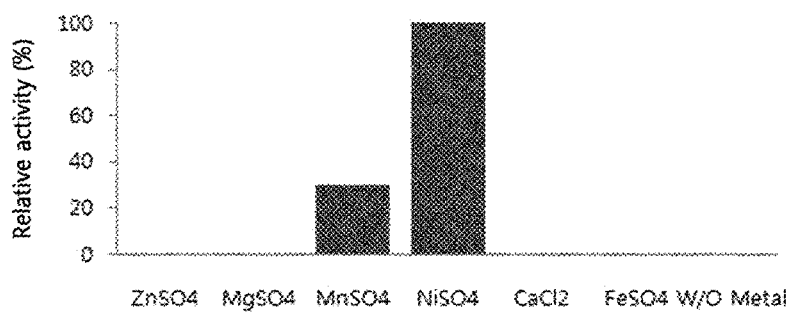
FIG. 5B is a graph showing fructose-4-epimerization activity of tagatose-biphosphate aldolase (CJ_RM_F4E) prepared in one embodiment of the present disclosure according to addition of metals.

As a result, the activity of CJ_RP_F4E was increased by addition of $NiSO_4$, indicating that nickel ion is able to increase the activity (FIG. 5A), and the activity of CJ_RM_F4E was increased by addition of $MnSO_4$ or $NiSO_4$, respectively, indicating that manganese ion or nickel ion is able to increase the activity of the recombinant enzyme of the present disclosure (FIG. 5B).

EXAMPLE 3

Production of Tagatose-Biphosphate Aldolase and Evaluation of its Activity

EXAMPLE 3-1

Production of Recombinant Expression Vector and Transformant Including Tagatose-Biphosphate Aldolase Gene The present inventors obtained information of a tagatose-biphosphate aldolase gene derived from *Limnochorda pilosa*

DSM 28787, and prepared a recombinant vector expressible in *E.coli* and a transformed microorganism.

More specifically, a nucleotide sequence of tagatose-biphosphate aldolase was selected from a nucleotide sequence of *Limnochorda pilosa*, which is registered in KEGG (Kyoto Encyclopedia of Genes and Genomes) and ENA (European Nucleotide Archive), and based on an amino acid sequence (SEQ ID NO: 11) and a nucleotide sequences (SEQ ID NO: 12) of tagatose-biphosphate aldolase CJ_LP_F4E derived from *Limnochorda pilosa*, pBT7-C-His-CJ_LP_F4E which is a recombinant expression vector containing the nucleotide sequence of the enzyme and expressible in *E.coli* was produced (Bioneer Corp., Korea).

The recombinant vector was transformed into *E.coli* BL21(DE3) by heat shock transformation (Sambrook and Russell: Molecular cloning, 2001), and frozen and stored in 50% glycerol. The transformant was designated as *E.coli* BL21(DE3)/CJ_LP_F4E, and deposited at the Korean Culture Center of Microorganisms (KCCM) which is an international depositary authority under the provisions of the Budapest Treaty on Aug. 11, 2017 with Accession No. KCCM12095P.

EXAMPLE 3-2

Production and Purification of Recombinant Enzyme

To obtain a recombinant enzyme of the present disclosure from *E.coli* BL21(DE3)/CJ_LP_F4E which is the transformant produced in Example 3-1, the transformant was seeded in a culture tube containing 5 mL of an LB liquid medium with ampicillin, and then seed culture was performed in a shaking incubator at 37° C. until absorbance at 600 nm reached 2.0. The culture obtained by the seed culture was seeded in a culture flask containing a liquid medium containing LB and lactose which is a protein expression regulator, and then main culture was performed. The seed culture and the main culture were performed under conditions of 180 rpm and 37° C. Then, the culture was centrifuged at 8,000 rpm and 4° C. for 20 minutes to recover cells. The recovered cells were washed with 50 mM Tris-HCl (pH 8.0) buffer twice and re-suspended in 50 mM $NaH_2PO_4$ (pH 8.0) buffer containing 10 mM imidazole and 300 mM NaCl. The re-suspended cells were disrupted using a sonicator. A cell lysate was centrifuged at 13,000 rpm and 4° C. for 20 minutes to take only a supernatant. The supernatant was purified by His-tag affinity chromatography, and 10 column volumes of 50 mM $NaH_2PO_4$ (pH 8.0) buffer containing 20 mM imidazole and 300 mM NaCl was applied to remove non-specifically bound proteins. Next, 50 mM $NaH_2PO_4$ (pH 8.0) buffer containing 250 mM imidazole and 300 mM NaCl was further applied to perform elution. Dialysis was performed using 50 mM Tris-HCl (pH 8.0) buffer to obtain CJ_LP_F4E which is a purified enzyme for enzyme characterization.

EXAMPLE 3-3

Evaluation of Activity of Recombinant Enzyme to Convert Fructose into Tagatose

To measure activity of CJ_LP_F4E which is the recombinant enzyme of the present disclosure obtained in Example 3-2, 50 mM Tris-HCl (pH 8.0), 1 mM $NiSO_4$, and 20 mg/mL of CJ_LP_F4E were added to 30% by weight of fructose, and allowed to react at 60° C. for 10 hours.

Figure 6:
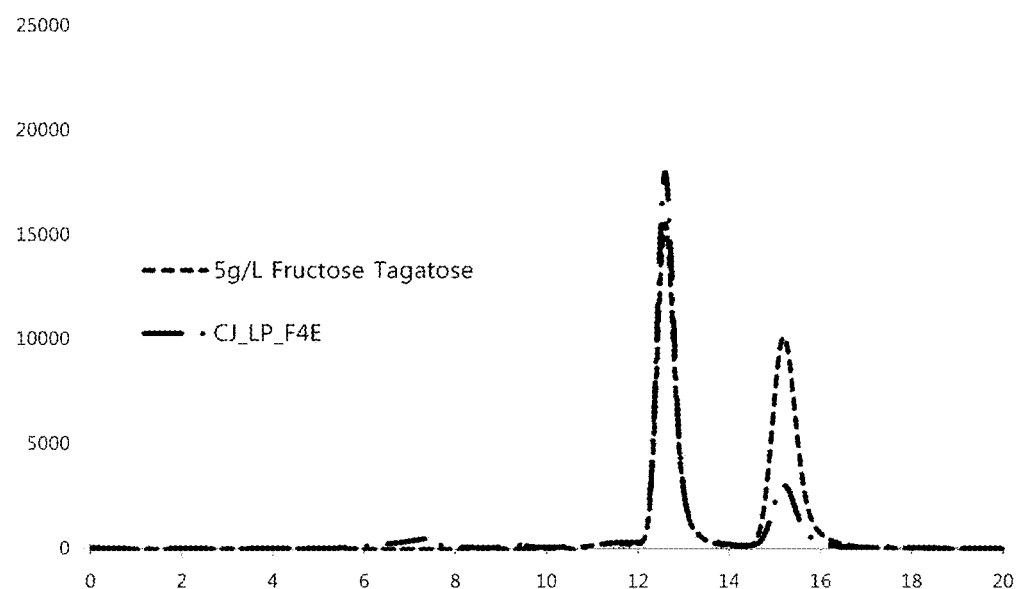
FIG. 6 is a graph of HPLC chromatography showing that tagatose-biphosphate aldolase (CJ_LP_F4E) prepared in one embodiment of the present disclosure has fructose-4-epimerase activity.

Further, fructose remaining after reaction and a product tagatose were quantified by HPLC. HPLC was performed by using Shodex Sugar SP0810 as a column, and a temperature of the column was 80° C., and water as a mobile phase was applied at a flow rate of 1 mL/min (FIG. 6).

As a result, it was confirmed that the conversion rate from fructose into tagatose by CJ_LP_F4E of the present disclosure was 9.5%.

EXAMPLE 3-4

Examination of Activity of Recombinant Enzyme According to Temperature

To examine an effect of temperature on the fructose-4-epimerization activity of the recombinant enzyme CJ_LP_F4E of the present disclosure prepared in Example 3-2, 1 mg/mL of CJ_LP_F4E was added to 50 mM Tris HCl (pH 8.0) buffer containing 10% by weight of fructose, and allowed to react at different temperatures of 45° C., 50° C., 55° C., 60° C., and 70° C. for 3 hours. Tagatose in each of the reacted solutions was quantified by HPLC.

Figure 7A:
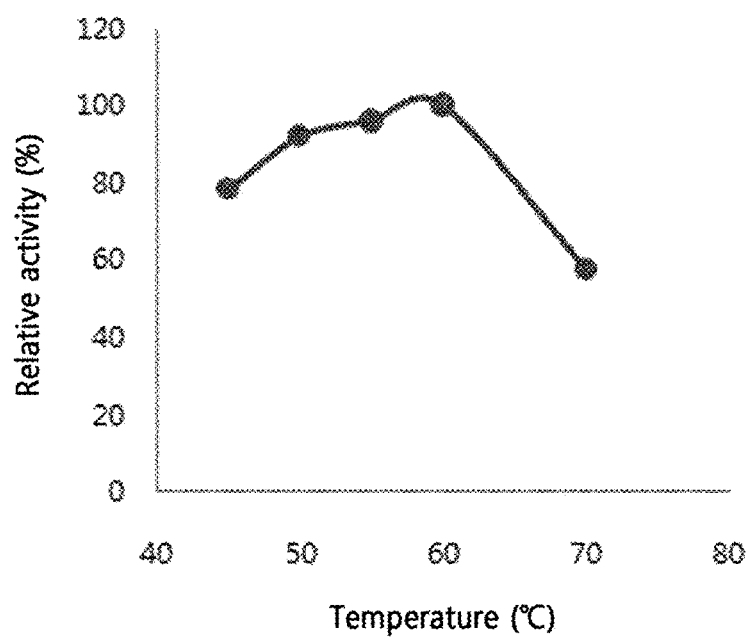
FIG. 7A is a graph showing fructose-4-epimerization activity of tagatose-biphosphate aldolase (CJ_LP_F4E) prepared in one embodiment of the present disclosure according to temperature changes.

As a result, CJ_LP_F4E of the present disclosure showed its maximum activity at 60° C., and maintained 50% or more of its maximum activity at 45° C. to 70° C. (FIG. 7A).

EXAMPLE 3-5

Examination of Activity of Recombinant Enzyme According to Addition of Metal Ion The known isomerases, e.g., glucose isomerase and arabinose isomerase, and epimerases, e.g., psicose 3-epimerase are known to require metal ions. Therefore, it was examined whether metal ions affect the fructose-4-epimerization activity of the recombinant enzyme CJ_LP_F4E prepared in Example 3-2.

More specifically, 2 mg/mL of CJ_LP_F4E and each 1 mM of various metal ions, $NiSO_4$, $CaCl_2$, $ZnSO_4$, $MgSO_4$, $MnSO_4$, $FeSO_4$, $CuSO_4$, or $(NH_4)_2SO_4$ were added to 50 mM Tris HCl (pH 8.0) buffer containing 10% by weight of fructose to measure the enzyme activity. Non-treatment of the metal ions was determined as a control group. Tagatose in each of the reacted solutions was quantified by HPLC.

Figure 7B:
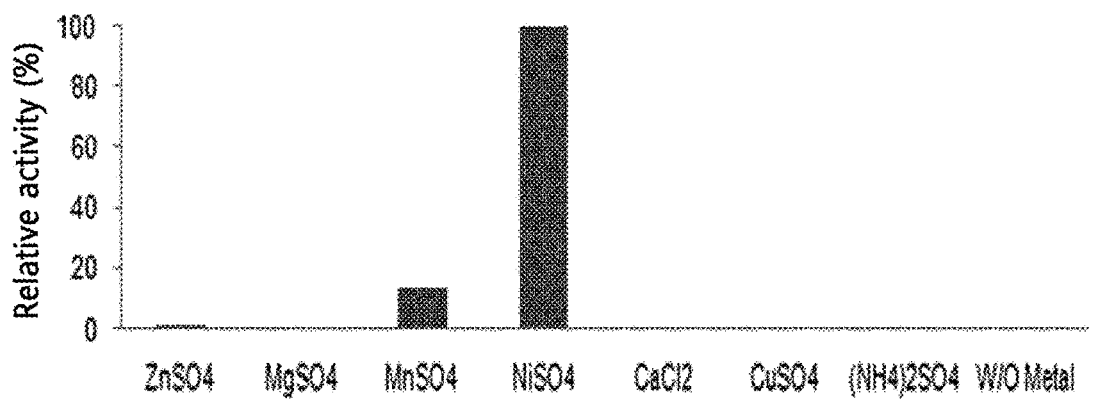
FIG. 7B is a graph showing fructose-4-epimerization activity of tagatose-biphosphate aldolase (CJ_LP_F4E) prepared in one embodiment of the present disclosure according to addition of metals.

As a result, the activity of CJ_LP_F4E of the present disclosure was increased by addition of $MnSO_4$ or $NiSO_4$, indicating that CJ_LP_F4E requires metal ions such as manganese ion or nickel ion. In particular, CJ_LP_F4E showed its maximum activity when $NiSO_4$ was added (FIG. 7B).

EXAMPLE 4

Production of Tagatose-Biphosphate Aldolase and Evaluation of its Activity

EXAMPLE 4-1

Production of Recombinant Vectors and Recombinant Microorganisms Including Tagatose-Biphosphate Aldolase Gene To identify a novel heat-resistant fructose-4-epimerase, information of tagatose-biphosphate aldolase genes derived from *Caldithrix abyssi* DSM 13497 and *Caldicellulosirup-*

*tor kronotskyensis* DSM 18902 was obtained to prepare vectors expressible in *E.coli* and transformed microorganisms.

In detail, a nucleotide sequence of tagatose-biphosphate aldolase was selected from nucleotide sequences of Caldithrix abyssi DSM 13497 and *Caldicellulosiruptor kronotskyensis* DSM 18902, which are registered in KEGG (Kyoto Encyclopedia of Genes and Genomes) and NCBI (National Center for Biotechnology Information), and based on amino acid sequences (SEQ ID NOS: 13 and 15) and nucleotide sequences (SEQ ID NOS: 14 and 16) of the microorganisms, pBT7-C-His-CJ_Cab_F4E and pBT7-C-His-CJ_Ckr_F4E which are recombinant vectors containing the nucleotide sequence of the enzyme and expressible in *E.coli* were produced (Bioneer Corp., Korea).

Each of the produced recombinant vectors was transformed into *E.coli* BL21(DE3) by heat shock transformation (Sambrook and Russell: Molecular cloning, 2001) to prepare recombinant microorganisms, which were then frozen and stored in 50% glycerol, respectively. The recombinant microorganisms were designated as *E.coli* BL21(DE3)/CJ_Cab_F4E and *E.coli* BL21(DE3)/CJ_Ckr_F4E, respectively and deposited at the Korean Culture Center of Microorganisms (KCCM) which is an international depositary authority under the provisions of the Budapest Treaty on Sep. 13, 2017 with Accession Nos. KCCM12107P and KCCM12108P, respectively.

EXAMPLE 4-2

Production and Purification of Recombinant Enzymes

To produce recombinant enzymes CJ_Cab_F4E and CJ_Ckr_F4E from *E.coli* BL21(DE3)/CJ_Cab_F4E and *E.coli* BL21(DE3)/CJ_Ckr_F4E which are the recombinant microorganisms produced in Example 4-1, each of the recombinant microorganisms was seeded in a culture tube containing 5 mL of an LB liquid medium with ampicillin antibiotic, and then seed culture was performed in a shaking incubator at 37° C. until absorbance at 600 nm reached 2.0. Each of the cultures obtained by the seed culture was seeded in a culture flask containing a liquid medium containing LB and lactose which is a protein expression regulator, and then main culture was performed. The seed culture and the main culture were performed under conditions of 180 rpm and 37° C. Then, each culture was centrifuged at 8,000 rpm and 4° C. for 20 minutes to recover cells. The recovered cells were washed with 50 mM Tris-HCl (pH 8.0) buffer twice and re-suspended in 50 mM $NaH_2PO_4$ (pH 8.0) buffer containing 10 mM imidazole and 300 mM NaCl. The re-suspended cells were disrupted using a sonicator. Cell lysates were centrifuged at 13,000 rpm and 4° C. for 20 minutes to take only supernatants. Each supernatant was purified by His-tag affinity chromatography, and 10 column volumes of 50 mM $NaH_2PO_4$ (pH 8.0) buffer containing 20 mM imidazole and 300 mM NaCl was applied to remove non-specifically bound proteins. Next, 50 mM $NaH_2PO_4$ (pH 8.0) buffer containing 250 mM imidazole and 300 mM NaCl was further applied to perform elution. Dialysis was performed using 50 mM Tris-HCl (pH 8.0) buffer to obtain CJ_Cab_F4E and CJ_Ckr_F4E which are purified enzymes for enzyme characterization.

EXAMPLE 4-3

Evaluation of Activity of Recombinant Enzyme to Convert Fructose into Tagatose

To measure fructose-4-epimerization activities of CJ_Cab_F4E and CJ_Ckr_F4E which are the recombinant enzymes obtained in Example 4-2, 50 mM Tris-HCl (pH 8.0), 1 mM $MnSO_4$, and 5 mg/mL of each of CJ_Cab_F4E and CJ_Ckr_F4E were added to 10% by weight of fructose, and allowed to react at 60° C. for 24 hours.

Further, fructose remaining after reaction and a product tagatose were quantified by HPLC. HPLC was performed by using Shodex Sugar SP0810 as a column, and a temperature of the column was 80° C., and water as a mobile phase was applied at a flow rate of 1 mL/min.

Figure 8A:
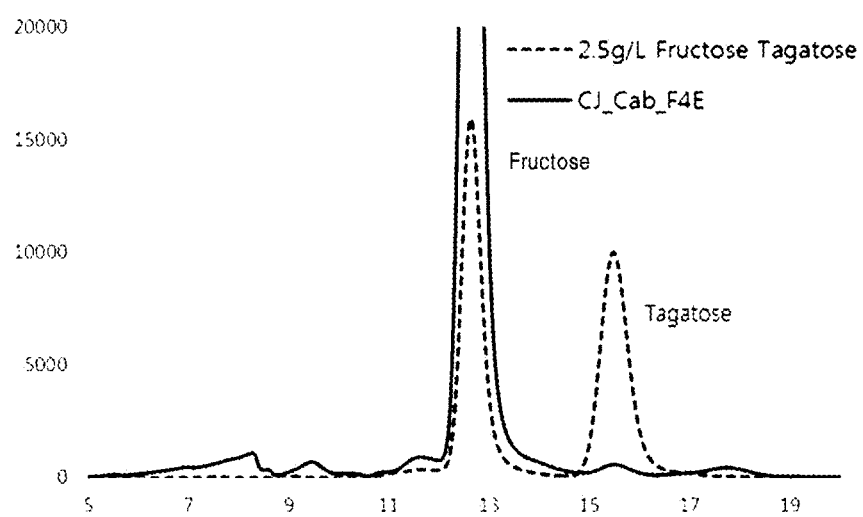
FIG. 8A is a graph of HPLC chromatography showing that tagatose-biphosphate aldolase (CJ_Cab_F4E) prepared in one embodiment of the present disclosure has fructose-4-epimerase activity.
Figure 8B:
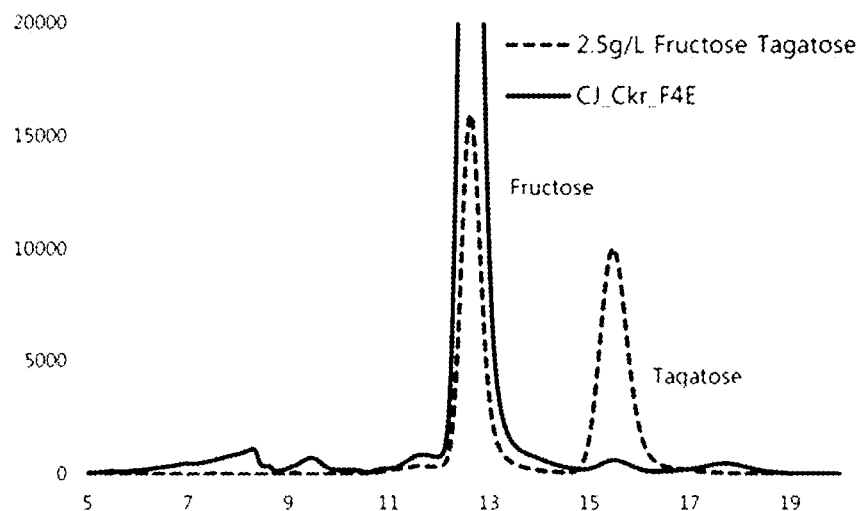
FIG. 8B is a graph of HPLC chromatography showing that CJ_Ckr_F4E prepared in one embodiment of the present disclosure has fructose-4-epimerase activity.

As a result, it was confirmed that the conversion rates from fructose into tagatose by the recombinant enzymes CJ_Cab_F4E and CJ_Ckr_F4E were 3.8% and 4.0%, respectively (FIGS. 8A and 8B).

EXAMPLE 4-4

Examination of Activities of Recombinant Enzymes According to Temperature

Figure 9A:
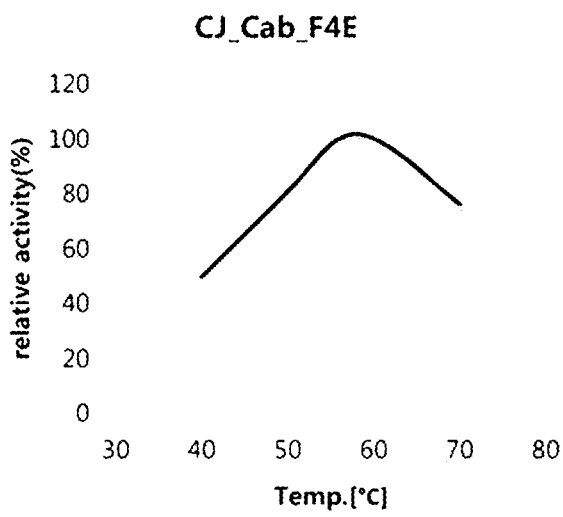
FIG. 9A is a graph showing fructose-4-epimerization activity of CJ_Cab_F4E prepared in one embodiment of the present disclosure according to a temperature.
Figure 9B:
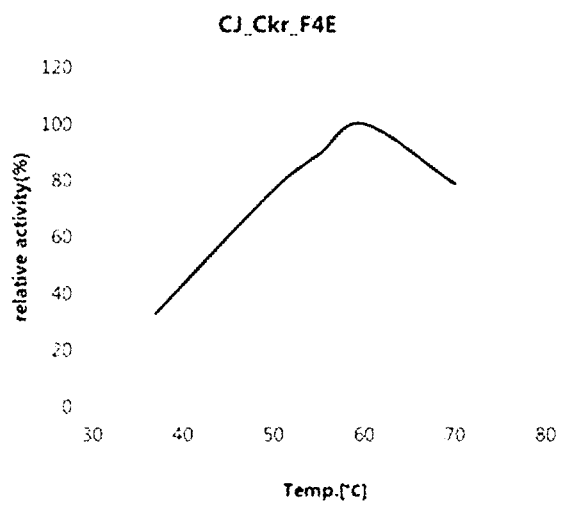
FIG. 9B is a graph showing fructose-4-epimerization activity of CJ_Ckr_F4E prepared in one embodiment of the present disclosure according to a temperature.

To examine an effect of temperature on the fructose-4-epimerization activities of the recombinant enzymes CJ_Cab_F4E and CJ_Ckr_F4E obtained in Example 4-2, each 5 mg/mL of CJ_Cab_F4E and CJ_Ckr_F4E was added to 50 mM Tris HCl (pH 8.0) buffer containing 5% by weight of fructose, and allowed to react at different temperatures of 37° C., 40° C., 50° C., 55° C., 60° C. and 70° C. for 5 hours. Tagatose in each of the reacted solutions was quantified by HPLC. As a result, CJ_Cab_F4E showed its maximum activity at 55° C., and CJ_Ckr_F4E showed its maximum activity at 60° C., and both of the enzymes showed 75% or more of their maximum activities at 50° C. to 70° C. (Table 1, FIGS. 9A and 9B).

TABLE 1

| | Relative activity (%) at each temperature | |
| --- | --- | --- |
| Section | CJ_Cab_F4E | CJ_CKr_F4E |
| 37° C. | — | 33.0 |
| 40° C. | 49.8 | — |
| 50° C. | 80.8 | 76.7 |
| 55° C. | 100.0 | 89.2 |
| 60° C. | 98.1 | 100.0 |
| 70° C. | 76.1 | 78.8 |

EXAMPLE 4-5

Examination of Activities of Recombinant Enzymes of the Present Disclosure According to Addition of Metal It was examined whether metals affect the fructose-4-epimerization activities of the recombinant enzymes CJ_Cab_F4E and CJ_Ckr_F4E prepared in Example 4-2.

In detail, each 5 mg/mL of CJ_Cab_F4E and CJ_Ckr_F4E and 1 mM of metal ions ($MgSO_4$ or $MnSO_4$) were added to 50 mM Tris HCl (pH 8.0) buffer containing 5% by weight of fructose, and allowed to react at 60° C. for 5 hours. Non-treatment of the metal ions was determined as a control group (w/o). Tagatose in each of the reacted solutions was quantified by HPLC.

Figure 10A:
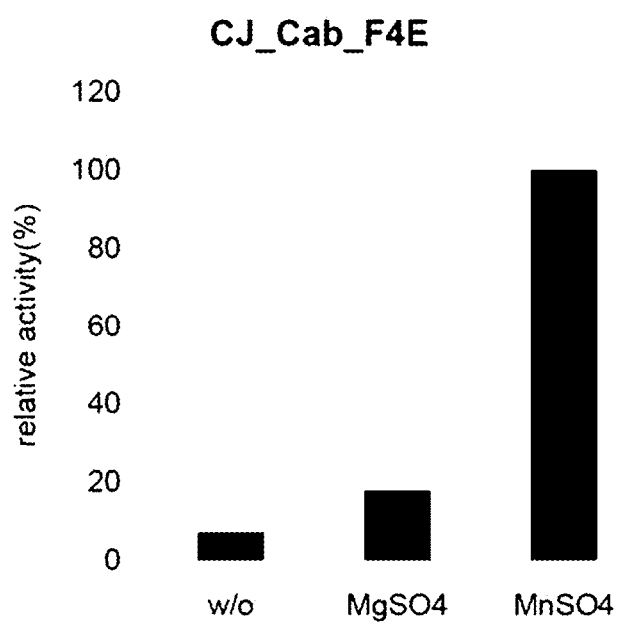
FIG. 10A is a graph showing fructose-4-epimerization activity of CJ_Cab_F4E prepared in one embodiment of the present disclosure according to addition of metals.
Figure 10B:
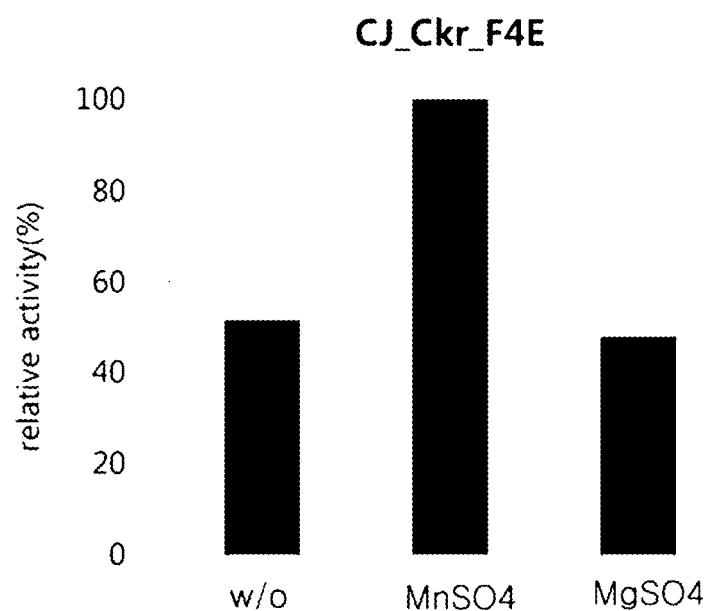
FIG. 10B is a graph showing fructose-4-epimerization activity of CJ_Ckr_F4E prepared in one embodiment of the present disclosure according to addition of metals.

As a result, the activity of CJ_Cab_F4E was increased about twice by addition of $MnSO_4$, and 10 times or more by addition of $MgSO_4$, indicating that manganese ion or magnesium ion (or a salt thereof) is able to increase the fructose-4-epimerization activity of CJ_Cab_F4E (FIG. 10A). Further, the activity of CJ_Ckr_F4E was similar to that of the control group by addition of MgSO$_4$, but its activity was increased about twice by addition of MnSO$_4$, indicating that manganese ion (or a salt thereof) is able to increase the fructose-4-epimerization activity of CJ_Ckr_F4E (FIG. 10B).

EXAMPLE 5

Production of Tagatose-Biphosphate Aldolase and Evaluation of its Activity

EXAMPLE 5-1

Production of Recombinant Vector and Recombinant Microorganism Including Tagatose-Biphosphate Aldolase Gene To identify a novel heat-resistant fructose-4-epimerase, information of a tagatose-biphosphate aldolase gene derived from *Caldilinea aerophila* was obtained to prepare a vector expressible in *E.coli* and a transformed microorganism.

Specifically, a nucleotide sequence of tagatose-biphosphate aldolase was selected from a nucleotide sequence of *Caldilinea aerophila*, which is registered in KEGG (Kyoto Encyclopedia of Genes and Genomes) and NCBI (National Center for Biotechnology Information), and based on an amino acid sequence (SEQ ID NO: 17) and a nucleotide sequences (SEQ ID NO: 18) of the microorganism, pET21a-CJ_CAE_F4E which is a recombinant vector containing the nucleotide sequence of the enzyme and expressible in *E.coli* was cloned.

To use the recombinant expression vector, PCR was performed using gnomic DNA of *Caldilinea aerophila* and primer 1: ATATACATATGTCAACACTTCGCCACAT-CATTTTGCGA (SEQ ID NO:21)and primer 2: TGGTGCTCGAGTCCAAGCAATGTAGCGGCGTCGTA (SEQ ID NO:22) under conditions of denaturation at 94° C. for 2 minutes, followed by 35 cycles of denaturation at 94° C. for 30 seconds, annealing at 65° C. for 30 seconds, elongation at 72° C. for 2 minutes, and then elongation at 72° C. for 5 minutes.

The recombinant vector was transformed into *E.coli* BL21(DE3) by heat shock transformation (Sambrook and Russell: Molecular cloning, 2001) to prepare a recombinant microorganism, and frozen and stored in 50% glycerol. The recombinant microorganism was designated as *E.coli* BL21 (DE3)/CJ_CAE_F4E, and deposited at the Korean Culture Center of Microorganisms (KCCM) which is an International Depositary Authority under the provisions of the Budapest Treaty on Mar. 23, 2018 with Accession No. KCCM 12233P.

EXAMPLE 5-2

Production and Purification of Recombinant Enzyme

To prepare a recombinant enzyme CJ_CAE_F4E from the recombinant microorganism *E.coli* BL21(DE3)/CJ_CAE_F4E produced in Example 5-1, the recombinant microorganism was seeded in a culture tube containing 5 mL of an LB liquid medium with ampicillin antibiotic, and then seed culture was performed in a shaking incubator at 37° C. until absorbance at 600 nm reached 2.0. The culture obtained by the seed culture was seeded in a culture flask containing a liquid medium containing LB and lactose which is a protein expression regulator, and then main culture was performed. The seed culture and the main culture were performed under conditions of 180 rpm and 37° C. Then, the culture was centrifuged at 8,000 rpm and 4° C. for 20 minutes to recover cells. The recovered cells were washed with 50 mM Tris-HCl (pH 8.0) buffer twice and suspended in 50 mM NaH$_2$PO$_4$ (pH 8.0) buffer containing 10 mM imidazole and 300 mM NaCl. The suspended cells were disrupted using a sonicator. A cell lysate was centrifuged at 13,000 rpm and 4° C. for 20 minutes to take only a supernatant. The supernatant was purified by His-tag affinity chromatography, and 10 column volumes of 50 mM NaH$_2$PO$_4$ (pH 8.0) buffer containing 20 mM imidazole and 300 mM NaCl was applied to remove non-specifically bound proteins. Next, 50 mM NaH$_2$PO$_4$ (pH 8.0) buffer containing 250 mM imidazole and 300 mM NaCl was further applied to perform elution. Dialysis was performed using 50 mM Tris-HCl (pH 8.0) buffer to obtain CJ_CAE_F4E which is a purified enzyme for enzyme characterization.

EXAMPLE 5-3

Evaluation of Activity of Recombinant Enzyme to Convert Fructose into Tagatose

To measure fructose-4-epimerization activity of CJ CAE F4E which is the recombinant enzyme obtained in Example 5-2, 50 mM Tris-HCl (pH 8.0), 1 mM MnSO$_4$, and 20 mg/mL of CJ_CAE_F4E were added to 10% by weight of fructose, and allowed to react at 60° C. for 24 hours.

Fructose remaining after reaction and a product tagatose were quantified by HPLC. HPLC was performed by using Shodex Sugar SP0810 as a column, and a temperature of the column was 80° C., and water as a mobile phase was applied at a flow rate of 1 mL/min.

Figure 11:
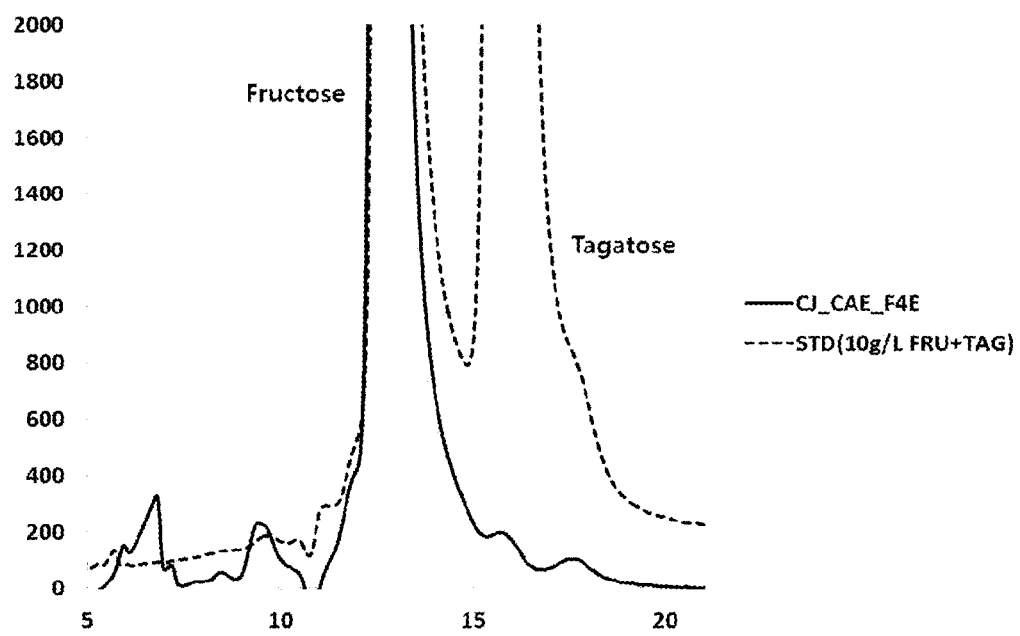
FIG. 11 is a graph of HPLC chromatography showing that CJ_CAE_F4E prepared in one embodiment of the present disclosure has fructose-4-epimerase activity.

As a result, it was confirmed that the conversion rate from fructose into tagatose by the recombinant enzyme CJ_CAE_F4E was 1.8% (FIG. 11).

EXAMPLE 6

Production of Tagatose-Biphosphate Aldolase and Evaluation of its Activity

EXAMPLE 6-1

Production of Recombinant Vector and Recombinant Microorganism Including Tagatose-Biphosphate Aldolase Gene To identify a novel heat-resistant fructose-4-epimerase, information of a tagatose-biphosphate aldolase gene derived from *Thermoanaerobacter thermohydrosulfuricus* was obtained to prepare a vector expressible in *E.coli* and a transformed microorganism.

In detail, a nucleotide sequence of tagatose-biphosphate aldolase was selected from a nucleotide sequence of *Thermoanaerobacter thermohydrosulfuricus*, which is registered in KEGG (Kyoto Encyclopedia of Genes and Genomes) and NCBI (National Center for Biotechnology Information), and based on an amino acid sequence (SEQ ID NO: 19) and a nucleotide sequences (SEQ ID NO: 20) of the microorganism, pBT7-C-His-CJ_TATH_F4E which is a recombinant vector containing the nucleotide sequence of the enzyme and expressible in *E.coli* was synthesized (Bioneer Corp., Korea).

The recombinant vector was transformed into *E.coli* BL21(DE3) by heat shock transformation (Sambrook and Russell: Molecular cloning, 2001) to prepare a recombinant microorganism, and frozen and stored in 50% glycerol. The recombinant microorganism was designated as *E.coli* BL21 (DE3)/CJ_TATH_F4E, and deposited at the Korean Culture Center of Microorganisms (KCCM) which is an International Depositary Authority under the provisions of the Budapest Treaty on Mar. 23, 2018 with Accession No. KCCM12234P.

EXAMPLE 6-2

Production and Purification of Recombinant Enzyme

To prepare a recombinant enzyme CJ_TATH_F4E from the recombinant microorganism *E.coli* BL21(DE3)/CJ_TATH_F4E produced in Example 6-1, the recombinant microorganism was seeded in a culture tube containing 5 mL of an LB liquid medium with ampicillin antibiotic, and then seed culture was performed in a shaking incubator at 37° C. until absorbance at 600 nm reached 2.0. The culture obtained by the seed culture was seeded in a culture flask containing a liquid medium containing LB and lactose which is a protein expression regulator, and then main culture was performed. The seed culture and the main culture were performed under conditions of 180 rpm and 37° C. Then, the culture was centrifuged at 8,000 rpm and 4° C. for 20 minutes to recover cells. The recovered cells were washed with 50 mM Tris-HCl (pH 8.0) buffer twice and suspended in 50 mM $NaH_2PO_4$ (pH 8.0) buffer containing 10 mM imidazole and 300 mM NaCl. The suspended cells were disrupted using a sonicator. A cell lysate was centrifuged at 13,000 rpm and 4° C. for 20 minutes to take only a supernatant. The supernatant was purified by His-tag affinity chromatography, and 10 column volumes of 50 mM $NaH_2PO_4$ (pH 8.0) buffer containing 20 mM imidazole and 300 mM NaCl was applied to remove non-specifically bound proteins. Next, 50 mM $NaH_2PO_4$ (pH 8.0) buffer containing 250 mM imidazole and 300 mM NaCl was further applied to perform elution. Dialysis was performed using 50 mM Tris-HCl (pH 8.0) buffer to obtain CJ_TATH_F4E which is a purified enzyme for enzyme characterization.

EXAMPLE 6-3

Evaluation of Activity of Recombinant Enzyme to Convert Fructose into Tagatose

To measure fructose-4-epimerization activity of CJ_TATH_F4E which is the recombinant enzyme obtained in Example 6-2, 50 mM Tris-HCl (pH 8.0), 1 mM $MnSO_4$, and 5 mg/mL of CJ_TATH_F4E were added to 30% by weight of fructose, and allowed to react at 60° C. for 24 hours.

Fructose remaining after reaction and a product tagatose were quantified by HPLC. HPLC was performed by using Shodex Sugar SP0810 as a column, and a temperature of the column was 80° C., and water as a mobile phase was applied at a flow rate of 1 mL/min.

Figure 12:
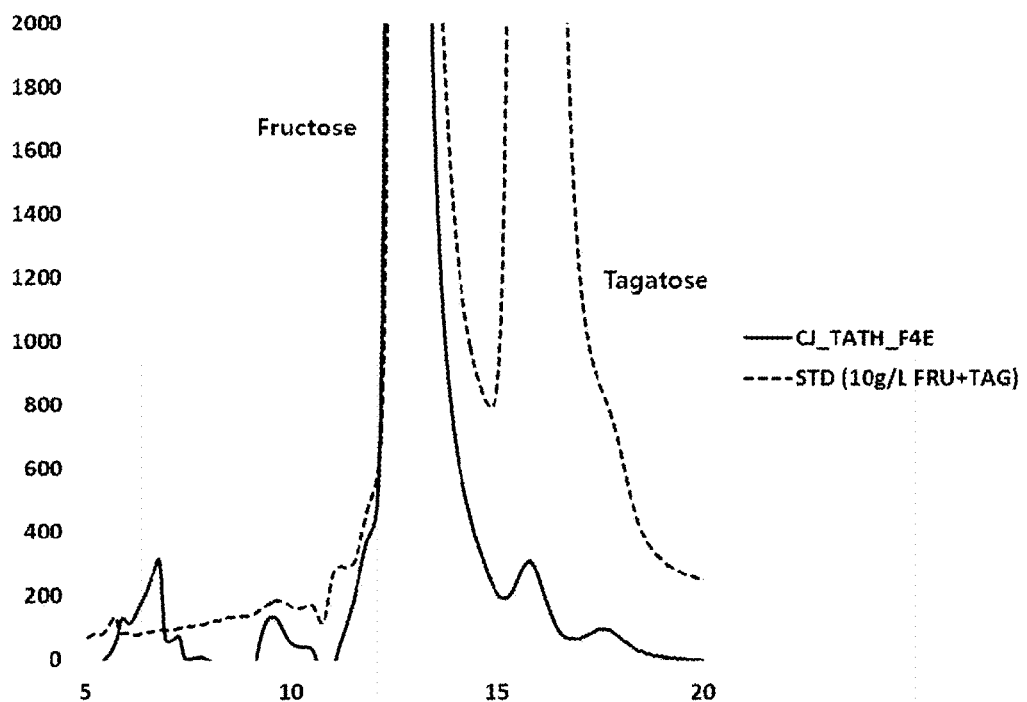
FIG. 12 is a graph of HPLC chromatography showing that CJ_TATH_F4E prepared in one embodiment of the present disclosure has fructose-4-epimerase activity.

As a result, it was confirmed that the conversion rate from fructose into tagatose by the recombinant enzyme CJ_TATH_F4E was 2.9% (FIG. 12).

EXAMPLE 7

Production of Tagatose-Biphosphate Aldolase and Evaluation of its Activity

EXAMPLE 7-1

Production of Recombinant Vector and Recombinant Microorganism Including Tagatose-Biphosphate Aldolase Gene To identify a novel heat-resistant fructose-4-epimerase, information of a tagatose-biphosphate aldolase gene derived from *Acidobacteriales bacterium* was obtained to prepare a vector expressible in *E.coli* and a transformed microorganism.

In detail, a nucleotide sequence of tagatose-biphosphate aldolase was selected from a nucleotide sequence of *Acidobacteriales bacterium*, which is registered in KEGG (Kyoto Encyclopedia of Genes and Genomes) and NCBI (National Center for Biotechnology Information), and based on an amino acid sequence (SEQ ID NO: 3) and a nucleotide sequences (SEQ ID NO: 4) of the microorganism, pBT7-C-His-CJ_AB_F4E which is a recombinant vector containing the nucleotide sequence of the enzyme and expressible in *E.coli* was synthesized (Bioneer Corp., Korea).

The recombinant vector was transformed into *E.coli* BL21(DE3) by heat shock transformation (Sambrook and Russell: Molecular cloning, 2001) to prepare a recombinant microorganism, and frozen and stored in 50% glycerol. The recombinant microorganism was designated as *E.coli* BL21 (DE3)/CJ_AB_F4E, and deposited at the Korean Culture Center of Microorganisms (KCCM) which is an International Depositary Authority under the provisions of the Budapest Treaty on Mar. 23, 2018 with Accession No. KCCM12237P.

EXAMPLE 7-2

Production and Purification of Recombinant Enzyme

To prepare a recombinant enzyme CJ_AB_F4E from the recombinant microorganism *E.coli* BL21(DE3)/CJ_AB_F4E produced in Example 7-1, the recombinant microorganism was seeded in a culture tube containing 5 mL of an LB liquid medium with ampicillin antibiotic, and then seed culture was performed in a shaking incubator at 37° C. until absorbance at 600 nm reached 2.0. The culture obtained by the seed culture was seeded in a culture flask containing a liquid medium containing LB and lactose which is a protein expression regulator, and then main culture was performed. The seed culture and the main culture were performed under conditions of 180 rpm and 37° C. Then, the culture was centrifuged at 8,000 rpm and 4° C. for 20 minutes to recover cells. The recovered cells were washed with 50 mM Tris-HCl (pH 8.0) buffer twice and suspended in 50 mM $NaH_2PO_4$ (pH 8.0) buffer containing 10 mM imidazole and 300 mM NaCl. The suspended cells were disrupted using a sonicator. A cell lysate was centrifuged at 13,000 rpm and 4° C. for 20 minutes to take only a supernatant. The supernatant was purified by His-tag affinity chromatography, and 10 column volumes of 50 mM $NaH_2PO_4$ (pH 8.0) buffer containing 20 mM imidazole and 300 mM NaCl was applied to remove non-specifically bound proteins. Next, 50 mM $NaH_2PO_4$ (pH 8.0) buffer containing 250 mM imidazole and 300 mM NaCl was further applied to perform elution. Dialysis was performed using 50 mM Tris-HCl (pH 8.0) buffer to obtain CJ_AB_F4E which is a purified enzyme for enzyme characterization.

EXAMPLE 7-3

Evaluation of Activity of Recombinant Enzyme to Convert Fructose into Tagatose

To measure fructose-4-epimerization activity of CJ_AB_F4E which is the recombinant enzyme obtained in Example 7-2, 50 mM Tris-HCl (pH 8.0), 1 mM $MnSO_4$, and 10 mg/mL of CJ_AB_F4E were added to 1% by weight of fructose, and allowed to react at 55° C. for 24 hours.

Fructose remaining after reaction and a product tagatose were quantified by HPLC. HPLC was performed by using Shodex Sugar SP0810 as a column, and a temperature of the column was 80° C., and water as a mobile phase was applied at a flow rate of 1 mL/min.

Figure 13:
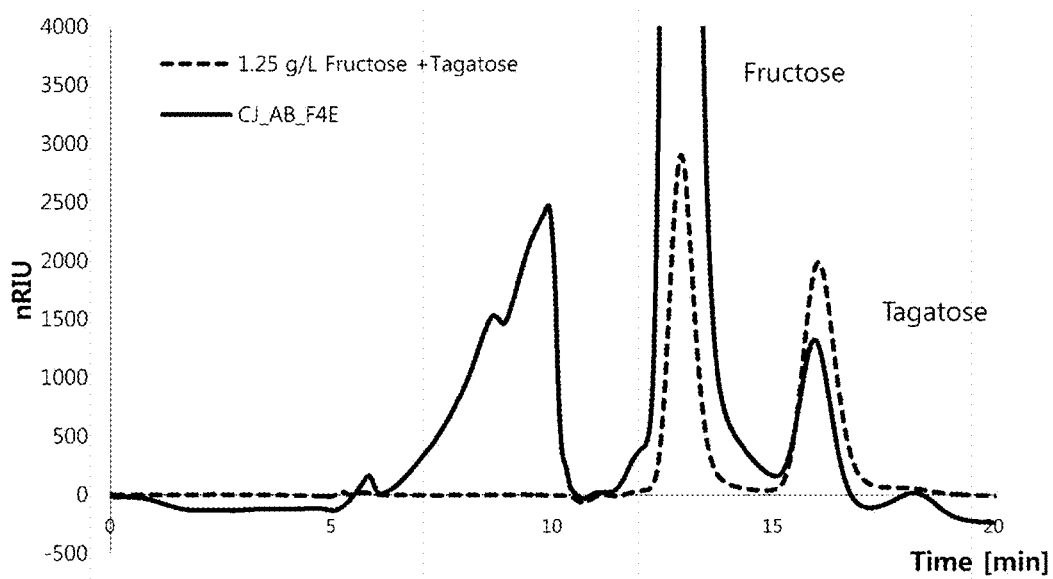
FIG. 13 is a graph of HPLC chromatography showing that CJ_AB_F4E prepared in one embodiment of the present disclosure has fructose-4-epimerase activity.

As a result, it was confirmed that the conversion rate from fructose into tagatose by the recombinant enzyme CJ_AB_F4E was 8% (FIG. 13

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the present disclosure is defined by the appended claims rather than by the description preceding them, and therefore all changes and modifications that fall within metes and bounds of the claims, or equivalents of such metes and bounds are therefore intended to be embraced by the claims.

Effect of the Invention

Tagatose-biphosphate aldolase which is a fructose-4-epimerase of the present disclosure has excellent heat resistance, produces tagatose at an industrial scale, and converts fructose as a common sugar into tagatose, and thus is economically feasible.

International Depositary Authority: Korean Culture Center of Microorganisms (foreign)
Accession No: KCCM11995P
Date of deposit: 20170320
International Depositary Authority: Korean Culture Center of Microorganisms (foreign)
Accession No: KCCM11999P
Date of deposit: 20170324
International Depositary Authority: Korean Culture Center of Microorganisms (foreign)
Accession No: KCCM12097P
Date of deposit: 20170811
International Depositary Authority: Korean Culture Center of Microorganisms (foreign)
Accession No: KCCM12096P
Date of deposit: 20170811
International Depositary Authority: Korean Culture Center of Microorganisms (foreign)
Accession No: KCCM12095P
Date of deposit: 20170811
International Depositary Authority: Korean Culture Center of Microorganisms (foreign)
Accession No: KCCM12107P
Date of deposit: 20170913
International Depositary Authority: Korean Culture Center of Microorganisms (foreign)
Accession No: KCCM12108P
Date of deposit: 20170913
International Depositary Authority: Korean Culture Center of Microorganisms (foreign)
Accession No: KCCM12233P
Date of deposit: 20180323
International Depositary Authority: Korean Culture Center of Microorganisms (foreign)
Accession No: KCCM12234P
Date of deposit: 20180323
International Depositary Authority: Korean Culture Center of Microorganisms (foreign)
Accession No: KCCM12237P
Date of deposit: 20180323

What is claimed is:

1. A method of producing tagatose in a single enzymatic step by directly converting fructose into tagatose, by contacting fructose with tagatose-biphosphate aldolase, a microorganism expressing the tagatose-biphosphate aldolase, or a culture of the microorganism comprising tagatose-biphosphate aldolase.

2. The method of producing tagatose of claim 1, wherein the contacting is performed under conditions of pH 5.0 to pH 9.0 and 30° C. to 80° C. for 0.5 hours to 48 hours.

* * * * *